US007910552B2

(12) United States Patent
Birr et al.

(10) Patent No.: US 7,910,552 B2
(45) Date of Patent: *Mar. 22, 2011

(54) BONE MORPHOGENETIC PROTEINS CONTAINING A HEPARIN BINDING SITE AND OSTEOGENIC DEVICES AND PHARMACEUTICAL PRODUCTS CONTAINING THEREOF

(75) Inventors: Elli Birr, Kempele (FI); Mari Ulmanen, Tampere (FI); Oili Hietala, Oulu (FI); Marja Juustila, Liminka (FI); Heli Korkala, Oulu (FI); Pekka Jalovaara, Oulu (FI)

(73) Assignee: BBS-Bioactive Bone Substitutes Oy, Oulu (FI)

( * ) Notice: Subject to any disclaimer, the term of this patent is extended or adjusted under 35 U.S.C. 154(b) by 461 days.

This patent is subject to a terminal disclaimer.

(21) Appl. No.: 11/921,069

(22) PCT Filed: May 26, 2006

(86) PCT No.: PCT/FI2006/050214
§ 371 (c)(1),
(2), (4) Date: Jan. 12, 2008

(87) PCT Pub. No.: WO2006/125868
PCT Pub. Date: Nov. 30, 2006

(65) Prior Publication Data
US 2010/0143433 A1    Jun. 10, 2010

(30) Foreign Application Priority Data

May 27, 2005    (FI) ..................... 20055256
May 27, 2005    (FI) ..................... 20055257
May 27, 2005    (FI) ..................... 20055258

(51) Int. Cl.
*A61K 38/16*    (2006.01)
*A61K 38/17*    (2006.01)
*A61K 38/18*    (2006.01)
*C12N 15/11*    (2006.01)
*C12N 15/12*    (2006.01)
*C12N 15/63*    (2006.01)
*C12N 1/21*     (2006.01)
*C12N 5/10*     (2006.01)

(52) U.S. Cl. .............. 514/16.7; 514/16.8; 514/16.9; 514/17.1; 514/21.2; 514/8.8; 530/350; 530/351; 530/300; 435/69.1; 435/320.1; 435/252.3; 435/254.11; 435/325; 536/23.1; 536/23.5

(58) Field of Classification Search ............... None
See application file for complete search history.

(56) References Cited

U.S. PATENT DOCUMENTS

| 5,106,626 A | 4/1992 | Parsons |
| 5,187,076 A | 2/1993 | Wozney et al. |
| 5,399,677 A | 3/1995 | Wolfman |
| 5,939,388 A | 8/1999 | Rosen |
| 2003/0187232 A1 | 10/2003 | Hubbell |

FOREIGN PATENT DOCUMENTS

| AU | 200021106 | 1/2000 |
| AU | 762387 | 6/2003 |
| EP | 1 131 087 | 9/2004 |
| WO | WO 90/03733 | 4/1990 |
| WO | WO 90/11366 | 10/1990 |
| WO | WO 92/05199 | 4/1992 |
| WO | WO 93/00049 | 1/1993 |
| WO | WO98/51354 | 11/1998 |
| WO | WO 2005/089826 | 9/2005 |

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
European search report in corresponding EP 06743556, Feb. 2009.
Ruppert R et al.,"Human bone morphogenetic protein 2 contains a heparin-binding site which modifies its biological activity", European Journal of Biochemistry, vol. 237, No. 1, Apr. 1, 1996, pp. 295-302, XP000891887.
De Noronha Pissarra, P. Recombinant DNA Proteins for the Biopharmaceutical Industry and the Future for *Escherichia Coli.* Business Briefing Pharma Outsourcing 2004 [Online], Jan. 204, [Retrieved Aug. 8, 2008] Retrieved From the Internet <URL.
Database Uniprod [Online] Oct. 1, 2002, Bone Morphogenetic Protein 6 (Fragment, *Equus caballus*), Retrieved From UNIPROT/EBI.
Database Uniprot [Online] Feb. 1, 1995 "Bone Morphogenetic Protein 6 Precursor (*Rattus norvegious*)".
Database NCBI/BENBANK Accession AAD27804 Apr. 27, 1999, Bone Morphogenetic Protein 7 Precursor.
Database EMBL EBI AC Q29607 Nov. 1, 1997, Bone Morphogenetic Pportein 4 Precursor BM -4 99% Identity With DEQ ID No. 1 in 116 AA Overlap (1-116:293-408) & Feng I.Q. et al Biochimica et Biophhysica ACTA.
Database EMBL EBL, AC Q 51419 May 10, 2005 Bone Morphogenetic Protein 4 Fragment 99% Identity With DEQ ID No. 1 in 116 AA Overlap 1-116 -274-389. Database EMBL EBI AC Q8MJV5, Oct. 1, 2002 Bone Morphogenetic Protein 4 99% Identity With SEQ ID No. 1 In 116 AA Overlap 1-116:294-409.
Database EMBL EBL AC AAE44686 Feb. 14, 2001 Sequence 2 From Patent US 608690 98% Identity With SEQ ID No. 1 In 116 AA Overlap 1-116:293-408 & US 6083690 A (Harris et al.).
Database EMBL EBL AC AAE08202, Sep. 29, 1999, Sequence 4 From Patent US 5804416 98% Identity With SEQ ID No. 1 In 116 AA Overlap (1-116:I116).
Database EMBL EBL AC AX356001 Feb. 6, 2002, Sequence 2 From Patent WO 0192298 98% Identity With SEQ ID No. 1 In 116 AA Overlap (1-116:I116).

(Continued)

*Primary Examiner* — Elizabeth C. Kemmerer
(74) *Attorney, Agent, or Firm* — Young & Thompson

(57) ABSTRACT he present invention relates to reindeer bone formation inducing protein called bone morphogenetic protein (BMP), such as BMP-6, containing a heparin binding site and nucleotide molecules encoding the proteins and host cells expressing the proteins. The present invention relates also to the use of the bone morphogenetic protein for treating disorders related to bone and cartilage formation. The present invention further relates to osteogenic devices and pharmaceutical compositions containing the protein.

24 Claims, 13 Drawing Sheets

OTHER PUBLICATIONS

Database EMBL EBI, AC AX722049 May 7, 2003, Sequence 2 From Patent EPO 1298140.0 98% Identity With SEQ ID No. 1 In AA Overlap 1-116:I116N.

Database EMBL EBI AC AF 300813 Oct. 13, 2000, Rangifer Tarandus Tarandus Bone Morphogenetic Protein 3B MRNA, Parital ODS 95.6% Identity With SEQ ID No. 1 In 138 AA Overlap (1-138:304-440.

Database EMBL EBI AC:CS031978 Mar. 13, 2005 Sequence 1484 From Patent WO 2005016962 A2.

Database EMBL EBI, AC ADQ19527, Aug 26, 2004 Human Soft Tissue Sarcomaupregulated Preotein SEQ ID No.1 In 138 AA Overlap (1-138:341-478 & WO 2004048938 A2 (Protein Design Labs Inc).

Database EMBL EBI AC ADN39338 Jun. 17, 2004 Cancer/Angiogenesis /Fibroisis Related Polypeptide SEQ ID No. B22 9.3.

5% Identity With SEQ ID No.1 In 138 AA Overlalp (1-138:341-478 & WO 03042661 A2.

Database EMBL EBI ACAAY92023 Jul. 19, 2000, Human Bone Morphogenetic Protein 3B BMP 3B.

Database EMBL EBI AC AA W06539 Mar. 12, 1997, Human Bone Morphogenetic Protein 10 93.5% Identity With SEQ ID No. 1 In 138 AA Overlap.

Database EMBL EBI AC AAR47587 Jul. 18, 1994 Rat Bone Formation Inducing Protein 93.5 Identity With SEQ ID No. 1 in 138 AA Overlap.

Database EMBL EBI AC ADH11577 Mar. 11, 2004 Human Bone Morphogenetic Proetein (BMP) Polypeptide #5, 93.5% Identity With SEQ ID No. 1 in 138 AA Overlap.

* cited by examiner

| | | | | | | | ccc | | cgg | | cgg | | | | |
|---|---|---|---|---|---|---|---|---|---|---|---|---|---|---|---|
| 1 | atg | gat | ccg | tcg | gcc | ccg | ggg | cgc | cgc | cgc | cag | cag | gcc | | 39 |
| | M | D | P | S | A | P | G | R | R | R | Q | Q | A | | |
| | | | | 5 | | | | | 10 | | | | | | |
| 40 | cgg | aac | cgc | tcc | acc | ccg | gcc | cag | gac | gtg | tcg | cgg | gcc | | 78 |
| | R | N | R | S | T | P | A | Q | D | V | S | R | A | | |
| | | 15 | | | | 20 | | | | 25 | | | | | |
| 79 | tcc | agc | gcc | tca | gac | tac | aac | agc | agc | gag | ctg | aaa | acg | | 117 |
| | S | S | A | S | D | Y | N | S | S | E | L | K | T | | |
| | | | 30 | | | | | 35 | | | | | | | |
| 118 | gcc | tgc | aga | aag | cac | gag | ctc | tac | gtg | agc | ttc | cag | gac | | 156 |
| | A | C | R | K | H | E | L | Y | V | S | F | Q | D | | |
| | 40 | | | | 45 | | | | 50 | | | | | | |
| 157 | ctg | ggg | tgg | cag | gac | tgg | atc | att | gcc | ccc | aag | ggc | tac | | 195 |
| | L | G | W | Q | D | W | I | I | A | P | K | G | Y | | |
| | | | 55 | | | | 60 | | | | | 65 | | | |
| 196 | gct | gcc | aac | tac | tgt | gac | gga | gaa | tgt | tcg | ttc | cct | ctc | | 234 |
| | A | A | N | Y | C | D | G | E | C | S | F | P | L | | |
| | | | | 70 | | | | | 75 | | | | | | |
| 235 | aac | gcg | cac | atg | aac | gcc | acc | aac | cac | gcc | atc | gtg | cag | | 273 |
| | N | A | H | M | N | A | T | N | H | A | I | V | Q | | |
| | | 80 | | | | 85 | | | | 90 | | | | | |
| | | | | | | | ccc | | | | ccc | | | | |
| 274 | acc | ctg | gtt | cac | ctc | atg | aac | ccg | gag | tac | gtc | ccg | aag | | 312 |
| | T | L | V | H | L | M | N | P | E | Y | V | P | K | | |
| | | | | 95 | | | | 100 | | | | | | | |
| 313 | ccg | tgc | tgt | gcg | ccc | acg | aaa | ctc | aac | gcc | atc | tcg | gtg | | 351 |
| | P | C | C | A | P | T | K | L | N | A | I | S | V | | |
| | 105 | | | | 110 | | | | | 115 | | | | | |
| 352 | ctc | tac | ttc | gac | gac | aac | tcc | aac | gtc | atc | ctg | aaa | aag | | 390 |
| | L | Y | F | D | D | N | S | N | V | I | L | K | K | | |
| | | | 120 | | | | 125 | | | | | 130 | | | |
| | | agg | | | | | cgg | | tgt | | | | | | |
| 391 | tac | cgc | aac | atg | gtc | gtc | cgc | gcc | tgc | ggc | tgc | cac | aag | | 429 |
| | Y | R | N | M | V | V | R | A | C | G | C | H | K | | |
| | | | | 135 | | | | | 140 | | | | | | |
| 430 | ctt | ggg | ccc | gaa | caa | aaa | ctc | atc | tca | gaa | gag | gat | ctg | | 468 |
| | L | G | P | E | Q | K | L | I | S | E | E | D | L | | |
| | | 145 | | | | | 150 | | | | 155 | | | | |
| 469 | aat | agc | gcc | gtc | gac | cat | cat | cat | cat | cat | cat | tga | | | 501 |
| | N | S | A | V | D | H | H | H | H | H | H | - | | | |
| | | | | 160 | | | | 165 | | | | | | | |

Fig. 5

| Pos | 1 | 2 | 3 | 4 | 5 | 6 | 7 | 8 | 9 | 10 | 11 | 12 | 13 | End |
|---|---|---|---|---|---|---|---|---|---|---|---|---|---|---|
| 1 | | atg M | gat D | ccg P | *caa* Q (5) | *gca* A | *aaa* K | *cat* H | *aaa* K | *cag* Q | *cgc* R (10) | *aaa* K | | 33 |
| 34 | *cgc* R | *ggt* G | *acc* T | tcg S (15) | gcc A | [ccc] ccg P | ggg G | [cgg] cgc R | cgc R (20) | [cgg] cgc R | cag Q | cag Q | gcc A | 72 |
| 73 | cgg R | aac N (25) | cgc R | tcc S | acc T | ccg P (30) | gcc A | cag Q | gac D | gtg V | tcg S (35) | cgg R | gcc A | 111 |
| 112 | tcc S | agc S | gcc A (40) | tca S | gac D | tac Y | aac N | agc S (45) | agc S | gag E | ctg L | aaa K | acg T (50) | 150 |
| 151 | gcc A | tgc C | aga R | aag K | cac H (55) | gag E | ctc L | tac Y | gtg V | agc S (60) | ttc F | cag Q | gac D | 189 |
| 190 | ctg L | ggg G (65) | tgg W | cag Q | gac D | tgg W | atc I (70) | att I | gcc A | ccc P | aag K | ggc G (75) | tac Y | 228 |
| 229 | gct A | gcc A | aac N | tac Y (80) | tgt C | gac D | gga G | gaa E | tgt C (85) | tcg S | ttc F | cct P | ctc L | 267 |
| 268 | aac N | gcg A (90) | cac H | atg M | aac N | gcc A (95) | acc T | aac N | cac H | gcc A | atc I (100) | gtg V | cag Q | 306 |
| 307 | acc T | ctg L | gtt V (105) | cac H | ctc L | atg M | aac N | [ccc] ccg P (110) | gag E | tac Y | gtc V | [ccc] ccg P | aag K (115) | 345 |
| 346 | ccg P | tgc C | tgt C | gcg A | ccc P (120) | acg T | aaa K | ctc L | aac N | gcc A (125) | atc I | tcg S | gtg V | 384 |
| 385 | ctc L | tac Y (130) | ttc F | gac D | gac D | aac N | tcc S (135) | aac N | gtc V | atc I | ctg L | aaa K (140) | aag K | 423 |
| 424 | tac Y | [agg] cgc R | aac N | atg M (145) | gtc V | gtc V | [cgg] cgc R | gcc A (150) | [tgt] tgc C | ggc G | tgc C | cac H | aag K | 462 |
| 463 | ctt L (155) | ggg G | ccc P | gaa E | caa Q | aaa K (160) | ctc L | atc I | tca S | gaa E | gag E (165) | gat D | ctg L | 501 |
| 502 | aat N | agc S | gcc A (170) | gtc V | gac D | cat H | cat H | cat H (175) | cat H | cat H | cat H | tga - | | 537 |

Fig. 6

| | | | | | | | | | | | | | |
|---|---|---|---|---|---|---|---|---|---|---|---|---|---|
| 1 | atg M | aaa K | tac Y | ctg L | ctg L 5 | ccg P | acc T | gct A | gct A | gct A 10 | ggt G | ctg L | ctg L | 39 |
| 40 | ctc L | ctc L 15 | gct A | gcc A | cag Q | ccg P | gcg A 20 | atg M | gcc A | atg M | gat D | atc I 25 | gga G | 78 |
| 79 | att I | aat N | tcg S | gat D 30 | ccg P | tcg S | gcc A | ccc/ccg P | ggg G 35 | cgg/cgc R | cgc R | cgg/cgc R | cag Q | 117 |
| 118 | cag Q | gcc A 40 | cgg R | aac N | cgc R | tcc S 45 | acc T | ccg P | gcc A | cag Q | gac D 50 | gtg V | tcg S | 156 |
| 157 | cgg R | gcc A | tcc S 55 | agc S | gcc A | tca S | gac D 60 | tac Y | aac N | agc S | agc S | gag E 65 | ctg L | 198 |
| 196 | aaa K | acg T | gcc A | tgc C | aga R 70 | aag K | cac H | gag E | ctc L | tac Y 75 | gtg V | agc S | ttc F | 234 |
| 235 | cag Q | gac D | ctg L 80 | ggg G | tgg W | cag Q | gac D 85 | tgg W | atc I | att I | gcc A | ccc P 90 | aag K | 273 |
| 274 | ggc G | tac Y | gct A | gcc A 95 | aac N | tac Y | tgt C | gac D | gga G 100 | gaa E | tgt C | tcg S | ttc F | 312 |
| 313 | cct P 105 | ctc L | aac N | gcg A | cac H | atg M 110 | aac N | gcc A | acc T | aac N | cac H 115 | gcc A | atc I | 351 |
| 352 | gtg V | cag Q | acc T 120 | ctg L | gtt V | cac H | ctc L 125 | atg M | aac N | ccc/ccg P | gag E | tac Y | gtc V 130 | 390 |
| 391 | ccc/ccg P | aag K | ccg P | tgc C 135 | tgt C | gcg A | ccc P | acg T | aaa K 140 | ctc L | aac N | gcc A | atc I | 429 |
| 430 | tcg S | gtg V 145 | ctc L | tac Y | ttc F | gac D 150 | gac D | aac N | tcc S | aac N | gtc V 155 | atc I | ctg L | 468 |
| 469 | aaa K | aag K | tac Y | agg/cgc R 160 | aac N | atg M | gtc V | gtc V | cgg/cgc R 165 | gcc A | tgt/tgc C | ggc G | tgc C | 507 |
| 508 | cac H 170 | aag K | ctt L | gcg A | gcc A | gca A 175 | ctc L | gag E | cac H | cac H | cac H 180 | cac H | cac H | 546 |
| 547 | cac H | tga | | | | | | | | | | | | 552 |

Figure 7

| | | | | | | | | | | | | | |
|---|---|---|---|---|---|---|---|---|---|---|---|---|---|
| 1 | atg M | aaa K | tac Y | ctg L | ctg L 5 | ccg P | acc T | gct A | gct A | gct A 10 | ggt G | ctg L | ctg L | 39 |
| 40 | ctc L | ctc L 15 | gct A | gcc A | cag Q | ccg P | gcg A 20 | atg M | gcc A | atg M | gat D | atc I 25 | gga G | 78 |
| 79 | att I | aat N | tcg S | gat D 30 | ccg P | caa Q | *gca* *A* | *aaa* *K* | *cat* *H* 35 | *aaa* *K* | *cag* *Q* | *cgc* *R* | *aaa* *K* | 117 |
| 118 | *cgc* *R* | *ggt* *G* 40 | *acc* *T* | tcg S | gcc A | ccc/ccg P 45 | ggg G | cgg/cgc R | cgc R | cgg/cgc R | cag Q 50 | cag Q | gcc A | 156 |
| 157 | cgg R | aac N | cgc R 55 | tcc S | acc T | ccg P | gcc A | cag Q 60 | gac D | gtg V | tcg S | cgg R | gcc A 65 | 195 |
| 196 | tcc S | agc S | gcc A | tca S | gac D 70 | tac Y | aac N | agc S | agc S | gag E 75 | ctg L | aaa K | acg T | 234 |
| 235 | gcc A | tgc C 80 | aga R | aag K | cac H | gag E | ctc L 85 | tac Y | gtg V | agc S | ttc F | cag Q 90 | gac D | 273 |
| 274 | ctg L | ggg G | tgg W | cag Q 95 | gac D | tgg W | atc I | att I | gcc A 100 | ccc P | aag K | ggc G | tac Y | 312 |
| 313 | gct A 105 | gcc A | aac N | tac Y | tgt C | gac D 110 | gga G | gaa E | tgt C | tcg S | ttc F 115 | cct P | ctc L | 351 |
| 352 | aac N | gcg A | cac H 120 | atg M | aac N | gcc A | acc T | aac N 125 | cac H | gcc A | atc I | gtg V | cag Q 130 | 390 |
| 391 | acc T | ctg L | gtt V | cac H 135 | ctc L | atg M | aac N | ccc/ccg P | gag E | tac Y 140 | gtc V | ccc/ccg P | aag K | 429 |
| 430 | ccg P | tgc C 145 | tgc C | gcg A | ccc P | acg T | aaa K 150 | ctc L | aac N | gcc A | atc I | tcg S 155 | gtg V | 468 |
| 469 | ctc L | tac Y | ttc F | gac D 160 | gac D | aac N | tcc S | aac N | gtc V 165 | atc I | ctg L | aaa K | aag K | 507 |
| 508 | tac Y | agg/cgc R 170 | aac N | atg M | gtc V | gtc V 175 | cgg/cgc R | gcc A | tgt/tgc C | ggc G | tgc C 180 | cac H | aag K | 546 |
| 547 | ctt L | gcg A | gcc A 185 | gca A | ctc L | gag E | cac H | cac H 190 | cac H | cac H | cac H | tga | 585 |

Fig. 8

| | | | | | | | | | | | | | |
|---|---|---|---|---|---|---|---|---|---|---|---|---|---|
| 1 | atg M | tct S | ggt G | tct S | cat H 5 | cat H | cat H | cat H | cat H | cat H 10 | agc S | agc S | 39 |
| 40 | ggc G | atc I | gaa E 15 | ggc G | cgc R | ggc G | tcg S | gcc A | ccc P 20 | ggg G | cgg R | cgc R | 78 |
| 79 | cgg R | cag Q 25 | cag Q | cgg R | aac N | cgc R 30 | tcc S | acc T | ccg P | gcc A | cag Q 35 | gac D | 117 |
| 118 | gtg V | tcg S | cgg R | tcc S 40 | agc S | gcc A | tca S | gac D 45 | tac Y | aac N | agc S | agc S | 156 |
| 157 | gag E | ctg L 50 | aaa K | gcc A | tgc C | aga R | aag K 55 | cac H | gag E | ctc L | tac Y | gtg V 60 | 195 |
| 196 | agc S | ttc F | cag Q | ctg L 65 | ggg G | tgg W | cag Q | gac D | tgg W 70 | atc I | att I | gcc A | 234 |
| 235 | ccc P | aag K | ggc G 75 | gct A | gcc A | aac N | tac Y | tgt C 80 | gac D | gga G | gaa E | tgt C | 273 |
| 274 | tcg S 85 | ttc F | cct P | aac N | gcg A | cac H 90 | atg M | aac N | gcc A | acc T | aac N 95 | cac H | 312 |
| 313 | gcc A | atc I | gtg V | acc T 100 | ctg L | gtt V | cac H | ctc L | atg M 105 | aac N | ccc P | gag E | 351 |
| 352 | tac Y | gtc V | ccc P 110 | ccg P | tgc C | tgt C | gcg A | ccc P 115 | acg T | aaa K | ctc L | aac N 120 | 390 |
| 391 | gcc A | atc I | tcg S | ctc L | tac Y 125 | ttc F | gac D | gac D | aac N | tcc S 130 | aac N | gtc V | 429 |
| 430 | atc I | ctg L | aaa K 135 | tac Y | agg R | aac N | atg M | gtc V 140 | gtc V | cgg R | gcc A | tgt C | 468 |
| 469 | ggc G | tgc C | cac H 145 | tag stop | gat D | ccg P 150 | taa stop | | | | | | 507 |

Fig. 9

| | | | | | | | | | | | | | |
|---|---|---|---|---|---|---|---|---|---|---|---|---|---|
| 1 | cgg Arg | atc Ile | tac Tyr | aag Lys | gac Asp 5 | tgt Cys | gtt Val | gtg Val | ggc Gly | agt Ser 10 | ttt Phe | aaa Lys | aac Asn | 39 |
| 40 | caa Gln | act Thr 15 | ttt Phe | ctt Leu | atc Ile | agc Ser | att Ile 20 | tac Tyr | caa Gln | gtc Val | tta Leu | cag Gln 25 | gag Glu | 78 |
| 79 | cat His | cag Gln | cac His | aga Arg 30 | gac Asp | tcc Ser | gac Asp | ctg Leu | ttt Phe 35 | ctg Leu | ctg Leu | ggc Gly | acg Thr | 117 |
| 118 | cgc Arg 40 | gcc Ala | gtg Val | tgg Trp | gcc Ala | tca Ser 45 | gag Glu | gcg Ala | ggc Gly | tgg Trp | ctg Leu 50 | gag Glu | ttc Phe | 156 |
| 157 | gac Asp | atc Ile | acg Thr 55 | gcc Ala | acc Thr | agc Ser | aac Asn | ctg Leu 60 | tgg Trp | gtc Val | ctg Leu | acc Thr | ccg Pro 65 | 195 |
| 196 | cag Gln | cac His | aac Asn | atg Met | ggg Gly 70 | ctg Leu | cag Gln | ctg Leu | agc Ser | gtg Val 75 | gtc Val | acg Thr | cgt Arg | 234 |
| 235 | gac Asp | ggg Gly 80 | ctc Leu | agc Ser | atc Ile | agc Ser | ccc Pro 85 | ggg Gly | gct Ala | gcg Ala | ggc Gly | ctg Leu 90 | gtg Val | 273 |
| 274 | ggc Gly | agg Arg | gac Asp | ggc Gly 95 | ccc Pro | tac Tyr | gac Asp | aag Lys | cag Gln 100 | ccc Pro | ttc Phe | atg Met | gtg Val | 312 |
| 313 | gcc Ala 105 | ttc Phe | ttc Phe | aag Lys | gcc Ala | agc Ser 110 | gag Glu | gcc Ala | cac His | gtg Val | cgc Arg 115 | agc Ser | gcc Ala | 351 |
| 352 | cgc Arg | tcg Ser | gcc Ala 120 | ccc Pro | ggg Gly | cgg Arg | cgc Arg | cgg Arg 125 | cag Gln | cag Gln | gcc Ala | cgg Arg | aac Asn 130 | 390 |
| 391 | cgc Arg | tcc Ser | acc Thr | ccg Pro 135 | gcc Ala | cag Gln | gac Asp | gtg Val | tcg Ser | cgg Arg 140 | gcc Ala | tcc Ser | agc Ser | 429 |
| 430 | gcc Ala | tca Ser 145 | gac Asp | tac Tyr | aac Asn | agc Ser | agc Ser 150 | gag Glu | ctg Leu | aaa Lys | acg Thr | gcc Ala 155 | tgc Cys | 468 |
| 469 | aga Arg | aag Lys | cac His 160 | gag Glu | ctc Leu | tac Tyr | gtg Val | agc Ser | ttc Phe 165 | cag Gln | gac Asp | ctg Leu | ggg Gly | 507 |
| 508 | tgg Trp 170 | cag Gln | gac Asp | tgg Trp | atc Ile | att Ile 175 | gcc Ala | ccc Pro | aag Lys | ggc Gly | tac Tyr 180 | gct Ala | gcc Ala | 546 |
| 547 | aac Asn | tac Tyr | tgt Cys 185 | gac Asp | gga Gly | gaa Glu | tgt Cys | tcg Ser 190 | ttc Phe | cct Pro | ctc Leu | aac Asn | gcg Ala 195 | 585 |

Fig. 10 A

| 586 | cac | atg | aac | gcc | acc | aac | cac | gcc | atc | gtg | cag | acc | ctg | 624 |
|---|---|---|---|---|---|---|---|---|---|---|---|---|---|---|
|  | His | Met | Asn | Ala | Thr | Asn | His | Ala | Ile | Val | Gln | Thr | Leu |  |
|  |  |  |  |  | 200 |  |  |  |  | 205 |  |  |  |  |

| 625 | gtt | cac | ctc | atg | aac | ccc | gag | tac | gtc | ccc | aag | ccg | tgc | 663 |
|---|---|---|---|---|---|---|---|---|---|---|---|---|---|---|
|  | Val | His | Leu | Met | Asn | Pro | Glu | Tyr | Val | Pro | Lys | Pro | Cys |  |
|  |  |  | 210 |  |  |  | 215 |  |  |  | 220 |  |  |  |

| 664 | tgt | gcg | ccc | acg | aaa | ctc | aac | gcc | atc | tcg | gtg | ctc | tac | 702 |
|---|---|---|---|---|---|---|---|---|---|---|---|---|---|---|
|  | Cys | Ala | Pro | Thr | Lys | Leu | Asn | Ala | Ile | Ser | Val | Leu | Tyr |  |
|  |  |  |  | 225 |  |  |  |  | 230 |  |  |  |  |  |

| 703 | ttc | gac | gac | aac | tcc | aac | gtc | atc | ctg | aaa | aag | tac | agg | 741 |
|---|---|---|---|---|---|---|---|---|---|---|---|---|---|---|
|  | Phe | Asp | Asp | Asn | Ser | Asn | Val | Ile | Leu | Lys | Lys | Tyr | Arg |  |
|  | 235 |  |  |  | 240 |  |  |  |  | 245 |  |  |  |  |

| 742 | aac | atg | gtc | gtc | cgg | gcc | tgt | ggc | tgc | cac | taa | 771 |
|---|---|---|---|---|---|---|---|---|---|---|---|---|
|  | Asn | Met | Val | Val | Arg | Ala | Cys | Gly | Cys | His | stop |  |
|  |  | 250 |  |  |  |  | 255 |  |  |  |  |  |

SEQUENCE LISTING

<160> NUMBER OF SEQ ID NOS: 69

<210> SEQ ID NO 1
<211> LENGTH: 139
<212> TYPE: PRT
<213> ORGANISM: Rangifer tarandus

<400> SEQUENCE: 1

```
Ser Ala Pro Gly Arg Arg Gln Gln Ala Arg Asn Arg Ser Thr Pro
1               5                   10                  15

Ala Gln Asp Val Ser Arg Ala Ser Ser Ala Ser Asp Tyr Asn Ser Ser
            20                  25                  30

Glu Leu Lys Thr Ala Cys Arg Lys His Glu Leu Tyr Val Ser Phe Gln
        35                  40                  45

Asp Leu Gly Trp Gln Asp Trp Ile Ile Ala Pro Lys Gly Tyr Ala Ala
    50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135
```

<210> SEQ ID NO 2
<211> LENGTH: 118
<212> TYPE: PRT
<213> ORGANISM: Rangifer tarandus

<400> SEQUENCE: 2

```
Arg Ile Tyr Lys Asp Cys Val Val Gly Ser Phe Lys Asn Gln Thr Phe
1               5                   10                  15

Leu Ile Ser Ile Tyr Gln Val Leu Gln Glu His Gln His Arg Asp Ser
            20                  25                  30

Asp Leu Phe Leu Leu Gly Thr Arg Ala Val Trp Ala Ser Glu Ala Gly
        35                  40                  45

Trp Leu Glu Phe Asp Ile Thr Ala Thr Ser Asn Leu Trp Val Leu Thr
    50                  55                  60

Pro Gln His Asn Met Gly Leu Gln Leu Ser Val Val Thr Arg Asp Gly
65                  70                  75                  80

Leu Ser Ile Ser Pro Gly Ala Ala Gly Leu Val Gly Arg Asp Gly Pro
                85                  90                  95

Tyr Asp Lys Gln Pro Phe Met Val Ala Phe Phe Lys Ala Ser Glu Ala
            100                 105                 110

His Val Arg Ser Ala Arg
        115
```

-continued

<210> SEQ ID NO 3
<211> LENGTH: 138
<212> TYPE: PRT
<213> ORGANISM: Rangifer tarandus

<400> SEQUENCE: 3

Arg Lys Lys Gly Gln Asp Val Phe Met Ala Ser Ser Gln Val Leu Asp
1               5                   10                  15

Phe Asp Glu Lys Thr Met Gln Lys Ala Arg Lys Lys Gln Trp Asp Glu
            20                  25                  30

Pro Arg Val Cys Ser Arg Arg Tyr Leu Lys Val Asp Phe Ala Asp Ile
        35                  40                  45

Gly Trp Asn Glu Trp Ile Ile Ser Pro Lys Ser Phe Asp Ala Tyr Tyr
    50                  55                  60

Cys Ser Gly Ala Cys Glu Phe Pro Met Pro Lys Met Val Arg Pro Ser
65                  70                  75                  80

Asn His Ala Thr Ile Gln Ser Ile Val Arg Ala Val Gly Ile Val Pro
                85                  90                  95

Gly Ile Pro Glu Pro Cys Cys Val Pro Asp Lys Met Ser Ser Leu Gly
            100                 105                 110

Val Leu Phe Leu Asp Glu Asn Arg Asn Val Val Leu Lys Val Tyr Pro
        115                 120                 125

Asn Met Ser Val Glu Thr Cys Ala Cys Gln
    130                 135

<210> SEQ ID NO 4
<211> LENGTH: 116
<212> TYPE: PRT
<213> ORGANISM: Rangifer tarandus

<400> SEQUENCE: 4

Ser Pro Lys His His Pro Gln Arg Ala Arg Lys Lys Asn Lys Asn Cys
1               5                   10                  15

Arg Arg His Ser Pro Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45

Cys Pro Phe Pro Leu Ala Asp His Leu Asn Ser Thr Asn His Ala Ile
    50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
        115

<210> SEQ ID NO 5
<211> LENGTH: 10
<212> TYPE: PRT
<213> ORGANISM: Rangifer tarandus

<400> SEQUENCE: 5

Ala Lys His Lys Gln Arg Lys Arg Gly Thr
1               5                   10

<210> SEQ ID NO 6

```
<211> LENGTH: 11
<212> TYPE: PRT
<213> ORGANISM: Rangifer tarandus

<400> SEQUENCE: 6

Gln Ala Lys His Lys Gln Arg Lys Arg Gly Thr
1               5                   10

<210> SEQ ID NO 7
<211> LENGTH: 139
<212> TYPE: PRT
<213> ORGANISM: Homo sapiens

<400> SEQUENCE: 7

Ser Ala Ser Ser Arg Arg Gln Gln Ser Arg Asn Arg Ser Thr Gln
1               5                   10                  15

Ser Gln Asp Val Ala Arg Val Ser Ala Ser Asp Tyr Asn Ser Ser
                20                  25                  30

Glu Leu Lys Thr Ala Cys Arg Lys His Glu Leu Tyr Val Ser Phe Gln
                35                  40                  45

Asp Leu Gly Trp Gln Asp Trp Ile Ile Ala Pro Lys Gly Tyr Ala Ala
    50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
                100                 105                 110

Ser Val Leu Tyr Phe Asp Asp Asn Ser Asn Val Ile Leu Lys Lys Tyr
                115                 120                 125

Arg Asn Met Val Val Arg Ala Cys Gly Cys His
        130                 135

<210> SEQ ID NO 8
<211> LENGTH: 139
<212> TYPE: PRT
<213> ORGANISM: Bos taurus

<400> SEQUENCE: 8

Ser Ala Pro Gly Arg Arg Gln Gln Ala Arg Asn Ala Ser Thr Pro
1               5                   10                  15

Ala Gln Asp Val Ser Arg Ala Ser Ser Ala Ser Asp Tyr Asn Ser Ser
                20                  25                  30

Glu Leu Lys Thr Ala Cys Arg Lys His Glu Leu Tyr Val Ser Phe Gln
                35                  40                  45

Asp Leu Gly Trp Gln Asp Trp Ile Ile Ala Pro Lys Gly Tyr Ala Ala
    50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
                100                 105                 110

Ser Val Leu Tyr Phe Asp Asp Asn Ser Asn Val Ile Leu Lys Lys Tyr
                115                 120                 125

Arg Asn Met Val Val Arg Ala Cys Gly Cys His
        130                 135
```

```
<210> SEQ ID NO 9
<211> LENGTH: 139
<212> TYPE: PRT
<213> ORGANISM: Rattus norvegicus

<400> SEQUENCE: 9

Ser Ala Ser Ser Arg Arg Gln Gln Ser Arg Asn Arg Ser Thr Gln
1               5                   10                  15

Ser Gln Asp Val Ser Arg Gly Ser Ser Ala Ser Asp Tyr Asn Ser Ser
                20                  25                  30

Glu Leu Lys Thr Ala Cys Lys Lys His Glu Leu Tyr Val Ser Phe Gln
            35                  40                  45

Asp Leu Gly Trp Gln Asp Trp Ile Ile Ala Pro Lys Gly Tyr Ala Ala
        50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135

<210> SEQ ID NO 10
<211> LENGTH: 139
<212> TYPE: PRT
<213> ORGANISM: Mus musculus

<400> SEQUENCE: 10

Ser Ala Ser Ser Arg Arg Gln Gln Ser Arg Asn Arg Ser Thr Gln
1               5                   10                  15

Ser Gln Asp Val Ser Arg Gly Ser Gly Ser Ser Asp Tyr Asn Gly Ser
                20                  25                  30

Glu Leu Lys Thr Ala Cys Lys Lys His Glu Leu Tyr Val Ser Phe Gln
            35                  40                  45

Asp Leu Gly Trp Gln Asp Trp Ile Ile Ala Pro Lys Gly Tyr Ala Ala
        50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135

<210> SEQ ID NO 11
<211> LENGTH: 138
<212> TYPE: PRT
<213> ORGANISM: Homo sapiens

<400> SEQUENCE: 11

Ala Ala Asn Lys Arg Lys Asn Gln Asn Arg Asn Lys Ser Ser Ser His
1               5                   10                  15
```

```
Gln Asp Ser Ser Arg Met Ser Ser Val Gly Asp Tyr Asn Thr Ser Glu
            20                  25                  30

Gln Lys Gln Ala Cys Lys Lys His Glu Leu Tyr Val Ser Phe Arg Asp
        35                  40                  45

Leu Gly Trp Gln Asp Trp Ile Ile Ala Pro Glu Gly Tyr Ala Ala Phe
    50                  55                  60

Tyr Cys Asp Gly Glu Cys Ser Phe Pro Leu Asn Ala His Met Asn Ala
65                  70                  75                  80

Thr Asn His Ala Ile Val Gln Thr Leu Val His Leu Met Phe Pro Asp
                85                  90                  95

His Val Pro Lys Pro Cys Cys Ala Pro Thr Lys Leu Asn Ala Ile Ser
            100                 105                 110

Val Leu Tyr Phe Asp Asp Ser Asn Val Ile Leu Lys Lys Tyr Arg
            115                 120                 125

Asn Met Val Val Arg Ser Cys Gly Cys His
        130                 135

<210> SEQ ID NO 12
<211> LENGTH: 139
<212> TYPE: PRT
<213> ORGANISM: Gallus gallus

<400> SEQUENCE: 12

Ala Ala Asn Asn Lys Arg Lys Asn Gln Asn Arg Asn Lys Ser Ser Ser
1               5                   10                  15

His Gln Glu Ser Ser Arg Met Pro Ser Val Gly Asp Tyr Asn Thr Ser
            20                  25                  30

Glu Gln Lys Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Phe Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Phe Pro
                85                  90                  95

Asp His Val Pro Lys Pro Cys Cys Ala Pro Thr Lys Leu Asn Ala Ile
            100                 105                 110

Ser Val Leu Tyr Phe Asp Asp Ser Ser Asn Val Ile Leu Lys Lys Tyr
            115                 120                 125

Arg Asn Met Val Val Arg Ser Cys Gly Cys His
        130                 135

<210> SEQ ID NO 13
<211> LENGTH: 138
<212> TYPE: PRT
<213> ORGANISM: Mus musculus

<400> SEQUENCE: 13

Ala Ala Ser Lys Arg Lys Asn Gln Asn Arg Asn Lys Ser Asn Ser His
1               5                   10                  15

Gln Asp Pro Ser Arg Met Pro Ser Ala Gly Asp Tyr Asn Thr Ser Glu
            20                  25                  30

Gln Lys Gln Ala Cys Lys Lys His Glu Leu Tyr Val Ser Phe Arg Asp
        35                  40                  45

Leu Gly Trp Gln Asp Trp Ile Ile Ala Pro Glu Gly Tyr Ala Ala Phe
    50                  55                  60

Tyr Cys Asp Gly Glu Cys Ser Phe Pro Leu Asn Ala His Met Asn Ala
```

```
                65                  70                  75                  80
Thr Asn His Ala Ile Val Gln Thr Leu Val His Leu Met Phe Pro Asp
                    85                  90                  95
His Val Pro Lys Pro Cys Cys Ala Pro Thr Lys Leu Asn Ala Ile Ser
                100                 105                 110
Val Leu Tyr Phe Asp Asp Ser Ser Asn Val Ile Leu Lys Lys Tyr Arg
            115                 120                 125
Asn Met Val Val Arg Ser Cys Gly Cys His
        130                 135

<210> SEQ ID NO 14
<211> LENGTH: 139
<212> TYPE: PRT
<213> ORGANISM: Xenopus laevis

<400> SEQUENCE: 14

Ser Ala Gly Gly Lys His Arg Asn Gln Asn Arg Ser Lys Ala Pro Lys
1               5                   10                  15
Ser Gln Glu Ala Leu Arg Val Ser Asn Ile Ala Glu Asn Ser Ser Thr
                20                  25                  30
Asp Gln Lys Gln Ala Cys Lys Lys His Glu Leu Tyr Val Ser Phe Lys
            35                  40                  45
Asp Leu Gly Trp Gln Asp Trp Ile Ile Ala Pro Glu Gly Tyr Ala Ala
        50                  55                  60
Phe Tyr Cys Glu Gly Glu Cys Ala Phe Pro Leu Asn Ser Tyr Met Asn
65                  70                  75                  80
Ala Thr Asn His Ala Ile Val Gln Thr Leu Val His Phe Ile Asn Pro
                    85                  90                  95
Asp Thr Val Pro Lys Pro Cys Cys Ala Pro Thr Gln Leu Asn Pro Ile
                100                 105                 110
Ser Val Leu Tyr Phe Asp Asp Ser Ser Asn Val Ile Leu Lys Lys Tyr
            115                 120                 125
Arg Asn Met Val Val Arg Ala Cys Gly Cys His
        130                 135

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
cggcatctac aaggactgtg ttggatggg                                       29

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
aatcaccgtc cgtgttccga ggcctg                                          26

<210> SEQ ID NO 17
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      Primer

<400> SEQUENCE: 17
ggatccgtcg gcccccgggc ggcgccggca g                                      31

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
cagcaggccc ggacaccgac ggtgttcgaa                                        30

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
ccgcggctcg gcccccgggc ggcgccggca g                                      31

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
cccggacacc gacggtgatc ctagg                                             25

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
ggtacctcgg cccccgggcg gcgccggcag                                        30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
cagcaggccc ggacaccgac ggtgttcgaa                                        30

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
```

-continued

Primer

<400> SEQUENCE: 23
ggatccgtcg gccccggggc gccgccgcca g                            31

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
cagcaggcgc ggacgccgac ggtgttcgaa                              30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
ggtacctcgg ccccggggcg ccgccgccag                              30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
cagcaggcgc ggacgccgac ggtgttcgaa                              30

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
taatacgact cactataggg cga                                     23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
cataagatat cacaatggat tta                                     23

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 29
agaggtatat attaatgtat cg                                              22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
gacttatcgc ggcagctggt a                                               21

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
taatacgact cactataggg cga                                             23

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
ggcgactcgt tattgatcg                                                  19

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
cctcatgaac ccggagtacg tcccgaagcc gtgctgtgcg                           40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
ggagtacttg ggcctcatgc agggcttcgg cacgacacgc                           40

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
```

-continued

```
cctgaaaaag taccgcaaca tggtcgtccg cgcc                                  34

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
ggactttttc atggcgttgt accagcaggc gcgg                                  34

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
cgggatccgc aagcaaaaca taaacagcgc aaacgcggta cccc                       44

<210> SEQ ID NO 38
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
gccctaggcg ttcgttttgt atttgtcgcc tttgcgccat gggg                       44

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
ccgcggctcg gccccccgggc ggcgc                                           25

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
ggtaccagga agaagggcca ggatgttttc                                       30

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
gacacctctg gacacggacg gttttcgaa                                        29
```

```
<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
ggtacccaat gggatgagcc acgggtc                                              27

<210> SEQ ID NO 43
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
gacacctctg gacacggacg gttttcgaa                                            29

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
caggtaccag ccccaagcat cacccacag                                            29

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 45
cacctcccta cacccacggc gttcgaa                                              27

<210> SEQ ID NO 46
<211> LENGTH: 166
<212> TYPE: PRT
<213> ORGANISM: Rangifer tarandus

<400> SEQUENCE: 46

Met Asp Pro Ser Ala Pro Gly Arg Arg Gln Gln Ala Arg Asn Arg
1               5                   10                  15

Ser Thr Pro Ala Gln Asp Val Ser Arg Ala Ser Ser Ala Ser Asp Tyr
                20                  25                  30

Asn Ser Ser Glu Leu Lys Thr Ala Cys Arg Lys His Glu Leu Tyr Val
            35                  40                  45

Ser Phe Gln Asp Leu Gly Trp Gln Asp Trp Ile Ile Ala Pro Lys Gly
        50                  55                  60

Tyr Ala Ala Asn Tyr Cys Asp Gly Glu Cys Ser Phe Pro Leu Asn Ala
65                  70                  75                  80

His Met Asn Ala Thr Asn His Ala Ile Val Gln Thr Leu Val His Leu
                85                  90                  95

Met Asn Pro Glu Tyr Val Pro Lys Pro Cys Cys Ala Pro Thr Lys Leu
                100                 105                 110
```

```
Asn Ala Ile Ser Val Leu Tyr Phe Asp Asp Asn Ser Asn Val Ile Leu
            115                 120                 125

Lys Lys Tyr Arg Asn Met Val Val Arg Ala Cys Gly Cys His Leu Gly
130                 135                 140

Pro Glu Gln Lys Leu Ile Ser Glu Glu Asp Leu Asn Ser Ala Val Asp
145                 150                 155                 160

His His His His His His
                165
```

<210> SEQ ID NO 47
<211> LENGTH: 178
<212> TYPE: PRT
<213> ORGANISM: Rangifer tarandus

<400> SEQUENCE: 47

```
Met Asp Pro Gln Ala Lys His Lys Gln Arg Lys Arg Gly Thr Ser Ala
1               5                   10                  15

Pro Gly Arg Arg Arg Gln Gln Ala Arg Asn Arg Ser Thr Pro Ala Gln
                20                  25                  30

Asp Val Ser Arg Ala Ser Ser Ala Ser Asp Tyr Asn Ser Ser Glu Leu
            35                  40                  45

Lys Thr Ala Cys Arg Lys His Glu Leu Tyr Val Ser Phe Gln Asp Leu
        50                  55                  60

Gly Trp Gln Asp Trp Ile Ile Ala Pro Lys Gly Tyr Ala Ala Asn Tyr
65                  70                  75                  80

Cys Asp Gly Glu Cys Ser Phe Pro Leu Asn Ala His Met Asn Ala Thr
                85                  90                  95

Asn His Ala Ile Val Gln Thr Leu Val His Leu Met Asn Pro Glu Tyr
            100                 105                 110

Val Pro Lys Pro Cys Cys Ala Pro Thr Lys Leu Asn Ala Ile Ser Val
        115                 120                 125

Leu Tyr Phe Asp Asp Asn Ser Asn Val Ile Leu Lys Lys Tyr Arg Asn
    130                 135                 140

Met Val Val Arg Ala Cys Gly Cys His Lys Leu Gly Pro Glu Gln Lys
145                 150                 155                 160

Leu Ile Ser Glu Glu Asp Leu Asn Ser Ala Val Asp His His His His
                165                 170                 175

His His
```

<210> SEQ ID NO 48
<211> LENGTH: 182
<212> TYPE: PRT
<213> ORGANISM: Rangifer tarandus

<400> SEQUENCE: 48

```
Met Lys Tyr Leu Leu Pro Thr Ala Ala Ala Gly Leu Leu Leu Leu Ala
1               5                   10                  15

Ala Gln Pro Ala Met Ala Met Asp Ile Gly Ile Asn Ser Asp Pro Ser
                20                  25                  30

Ala Pro Gly Arg Arg Arg Gln Gln Ala Arg Asn Arg Ser Thr Pro Ala
            35                  40                  45

Gln Asp Val Ser Arg Ala Ser Ser Ala Ser Asp Tyr Asn Ser Ser Glu
        50                  55                  60

Leu Lys Thr Ala Cys Arg Lys His Glu Leu Tyr Val Ser Phe Gln Asp
65                  70                  75                  80

Leu Gly Trp Gln Asp Trp Ile Ile Ala Pro Lys Gly Tyr Ala Ala Asn
```

```
                85                  90                  95
Tyr Cys Asp Gly Glu Cys Ser Phe Pro Leu Asn Ala His Met Asn Ala
                100                 105                 110

Thr Asn His Ala Ile Val Gln Thr Leu Val His Leu Met Asn Pro Glu
            115                 120                 125

Tyr Val Pro Lys Pro Cys Cys Ala Pro Thr Lys Leu Asn Ala Ile Ser
        130                 135                 140

Val Leu Tyr Phe Asp Asp Asn Ser Asn Val Ile Leu Lys Lys Tyr Arg
145                 150                 155                 160

Asn Met Val Val Arg Ala Cys Gly Cys His Lys Leu Ala Ala Ala Leu
                165                 170                 175

Glu His His His His His
            180

<210> SEQ ID NO 49
<211> LENGTH: 194
<212> TYPE: PRT
<213> ORGANISM: Rangifer tarandus

<400> SEQUENCE: 49

Met Lys Tyr Leu Leu Pro Thr Ala Ala Ala Gly Leu Leu Leu Leu Ala
1               5                   10                  15

Ala Gln Pro Ala Met Ala Met Asp Ile Gly Ile Asn Ser Asp Pro Gln
            20                  25                  30

Ala Lys His Lys Gln Arg Lys Arg Gly Thr Ser Ala Pro Gly Arg Arg
        35                  40                  45

Arg Gln Gln Ala Arg Asn Arg Ser Thr Pro Ala Gln Asp Val Ser Arg
    50                  55                  60

Ala Ser Ser Ala Ser Asp Tyr Asn Ser Ser Glu Leu Lys Thr Ala Cys
65                  70                  75                  80

Arg Lys His Glu Leu Tyr Val Ser Phe Gln Asp Leu Gly Trp Gln Asp
                85                  90                  95

Trp Ile Ile Ala Pro Lys Gly Tyr Ala Ala Asn Tyr Cys Asp Gly Glu
                100                 105                 110

Cys Ser Phe Pro Leu Asn Ala His Met Asn Ala Thr Asn His Ala Ile
            115                 120                 125

Val Gln Thr Leu Val His Leu Met Asn Pro Glu Tyr Val Pro Lys Pro
        130                 135                 140

Cys Cys Ala Pro Thr Lys Leu Asn Ala Ile Ser Val Leu Tyr Phe Asp
145                 150                 155                 160

Asp Asn Ser Asn Val Ile Leu Lys Lys Tyr Arg Asn Met Val Val Arg
                165                 170                 175

Ala Cys Gly Cys His Lys Leu Ala Ala Ala Leu Glu His His His His
            180                 185                 190

His His

<210> SEQ ID NO 50
<211> LENGTH: 147
<212> TYPE: PRT
<213> ORGANISM: Rangifer tarandus

<400> SEQUENCE: 50

Met Ser Gly Ser His His His His His His Ser Ser Gly Ile Glu Gly
1               5                   10                  15

Arg Gly Ser Ala Pro Gly Arg Arg Arg Gln Gln Arg Asn Arg Ser Thr
            20                  25                  30
```

Pro Ala Gln Asp Val Ser Arg Ser Ser Ala Ser Asp Tyr Asn Ser Ser
                35                  40                  45

Glu Leu Lys Ala Cys Arg Lys His Glu Leu Tyr Val Ser Phe Gln Leu
 50                  55                  60

Gly Trp Gln Asp Trp Ile Ile Ala Pro Lys Gly Ala Ala Asn Tyr Cys
 65                  70                  75                  80

Asp Gly Glu Cys Ser Phe Pro Asn Ala His Met Asn Ala Thr Asn His
                85                  90                  95

Ala Ile Val Thr Leu Val His Leu Met Asn Pro Glu Tyr Val Pro Pro
                100                 105                 110

Cys Cys Ala Pro Thr Lys Leu Asn Ala Ile Ser Leu Tyr Phe Asp Asp
                115                 120                 125

Asn Ser Asn Val Ile Leu Lys Tyr Arg Asn Met Val Val Arg Ala Cys
130                 135                 140

Gly Cys His
145

<210> SEQ ID NO 51
<211> LENGTH: 257
<212> TYPE: PRT
<213> ORGANISM: Rangifer tarandus

<400> SEQUENCE: 51

Arg Ile Tyr Lys Asp Cys Val Val Gly Ser Phe Lys Asn Gln Thr Phe
1               5                   10                  15

Leu Ile Ser Ile Tyr Gln Val Leu Gln Glu His Gln His Arg Asp Ser
                20                  25                  30

Asp Leu Phe Leu Leu Gly Thr Arg Ala Val Trp Ala Ser Glu Ala Gly
                35                  40                  45

Trp Leu Glu Phe Asp Ile Thr Ala Thr Ser Asn Leu Trp Val Leu Thr
 50                  55                  60

Pro Gln His Asn Met Gly Leu Gln Leu Ser Val Val Thr Arg Asp Gly
 65                  70                  75                  80

Leu Ser Ile Ser Pro Gly Ala Ala Gly Leu Val Gly Arg Asp Gly Pro
                85                  90                  95

Tyr Asp Lys Gln Pro Phe Met Val Ala Phe Phe Lys Ala Ser Glu Ala
                100                 105                 110

His Val Arg Ser Ala Arg Ser Ala Pro Gly Arg Arg Gln Gln Ala
                115                 120                 125

Arg Asn Arg Ser Thr Pro Ala Gln Asp Val Ser Arg Ala Ser Ser Ala
130                 135                 140

Ser Asp Tyr Asn Ser Ser Glu Leu Lys Thr Ala Cys Arg Lys His Glu
145                 150                 155                 160

Leu Tyr Val Ser Phe Gln Asp Leu Gly Trp Gln Asp Trp Ile Ile Ala
                165                 170                 175

Pro Lys Gly Tyr Ala Ala Asn Tyr Cys Asp Gly Glu Cys Ser Phe Pro
                180                 185                 190

Leu Asn Ala His Met Asn Ala Thr Asn His Ala Ile Val Gln Thr Leu
                195                 200                 205

Val His Leu Met Asn Pro Glu Tyr Val Pro Lys Pro Cys Cys Ala Pro
                210                 215                 220

Thr Lys Leu Asn Ala Ile Ser Val Leu Tyr Phe Asp Asp Asn Ser Asn
225                 230                 235                 240

Val Ile Leu Lys Lys Tyr Arg Asn Met Val Val Arg Ala Cys Gly Cys
                245                 250                 255

His

<210> SEQ ID NO 52
<211> LENGTH: 504
<212> TYPE: DNA
<213> ORGANISM: Rangifer tarandus

<400> SEQUENCE: 52

```
atggatccgt cggccccggg gcgccgccgc cagcaggccc ggaaccgctc caccccggcc      60
caggacgtgt cgcgggcctc cagcgcctca gactacaaca gcagcgagct gaaaacggcc     120
tgcagaaagc acgagctcta cgtgagcttc caggacctgg ggtggcagga ctggatcatt     180
gcccccaagg gctacgctgc caactactgt gacggagaat gttcgttccc tctcaacgcg     240
cacatgaacg ccaccaacca cgccatcgtg cagaccctgg ttcacctcat gaacccggag     300
tacgtcccga agccgtgctg tgcgcccacg aaactcaacg ccatctcggt gctctacttc     360
gacgacaact ccaacgtcat cctgaaaaag taccgcaaca tggtcgtccg cgcctgcggc     420
tgccacaagc ttgggcccga caaaaaactc atctcagaag aggatctgaa tagcgccgtc     480
gaccatcatc atcatcatca ttga                                            504
```

<210> SEQ ID NO 53
<211> LENGTH: 501
<212> TYPE: DNA
<213> ORGANISM: Rangifer tarandus

<400> SEQUENCE: 53

```
atggatccgc aagcaaaaca taaacagcgc aaacgcggta cctcggcccc ggggcgccgc      60
cgccagcagg cccggaaccg ctccaccccg gcccaggacg tgtcgcgggc ctccagcgcc     120
tcagactaca acagcagcga gctgaaaacg gcctgcagaa agcacgagct ctacgtgagc     180
ttccaggacc tggggtggca ggactggatc attgccccca agggctacgc tgccaactac     240
tgtgacggag aatgttcgtt ccctctcaac gcgcacatga acgccaccaa ccacgccatc     300
gtgcagaccc tggttcacct catgaacccg gagtacgtcc cgaagccgtg ctgtgcgccc     360
acgaaactca acgccatctc ggtgctctac ttcgacgaca actccaacgt catcctgaaa     420
aagtaccgca acatggtcgt ccgcgcctgc ggctgccaca agcttgggcc cgaacaaaaa     480
ctcatctcag aagaggatct g                                               501
```

<210> SEQ ID NO 54
<211> LENGTH: 546
<212> TYPE: DNA
<213> ORGANISM: Rangifer tarandus

<400> SEQUENCE: 54

```
atgaaatacc tgctgccgac cgctgctgct ggtctgctgc tcctcgctgc ccagccggcg      60
atggccatgg atatcggaat taattcggat ccgtcggccc cggggcgccg ccgccagcag     120
gcccggaacc gctccacccc ggcccaggac gtgtcgcggg cctccagcgc ctcagactac     180
aacagcagcg agctgaaaac ggcctgcaga aagcacgagc tctacgtgag cttccaggac     240
ctggggtggc aggactggat cattgccccc aagggctacg ctgccaacta ctgtgacgga     300
gaatgttcgt tccctctcaa cgcgcacatg aacgccacca ccacgccat cgtgcagacc     360
ctggttcacc tcatgaaccc ggagtacgtc cgaagccgt gctgtgcgcc cacgaaactc     420
aacgccatct cggtgctcta cttcgacgac aactccaacg tcatcctgaa aaagtaccgc     480
aacatggtcg tccgcgcctg cggctgccac aagcttgcgg ccgcactcga gcaccaccac     540
```

```
caccac                                                              546

<210> SEQ ID NO 55
<211> LENGTH: 585
<212> TYPE: DNA
<213> ORGANISM: Rangifer tarandus

<400> SEQUENCE: 55
atgaaatacc tgctgccgac cgctgctgct ggtctgctgc tcctcgctgc ccagccggcg    60
atggccatgg atatcggaat taattcggat ccgcaagcaa acataaaca gcgcaaacgc    120 ggtacctcgg ccccggggcg ccgccgccag caggcccgga accgctccac cccggcccag    180
gacgtgtcgc gggcctccag cgcctcagac tacaacagca gcgagctgaa aacggcctgc    240
agaaagcacg agctctacgt gagcttccag gacctgggt ggcaggactg gatcattgcc     300
cccaagggct acgctgccaa ctactgtgac ggagaatgtt cgttccctct caacgcgcac    360
atgaacgcca ccaaccacgc catcgtgcag accctggttc acctcatgaa cccggagtac    420
gtcccgaagc cgtgctgtgc gcccacgaaa ctcaacgcca tctcggtgct ctacttcgac    480
gacaactcca acgtcatcct gaaaaagtac cgcaacatgg tcgtccgcgc ctgcggctgc    540
cacaagcttg cggccgcact cgagcaccac caccaccacc actga                   585

<210> SEQ ID NO 56
<211> LENGTH: 453
<212> TYPE: DNA
<213> ORGANISM: Rangifer tarandus

<400> SEQUENCE: 56
atgtctggtt ctcatcatca tcatcatcat agcagcggca tcgaaggccg cggctcggcc    60
cccgggcggc gccggcagca gcggaaccgc tccaccccgg cccaggacgt gtcgcggtcc    120
agcgcctcag actacaacag cagcgagctg aaagcctgca gaaagcacga gctctacgtg    180
agcttccagc tggggtggca ggactggatc attgccccca agggcgctgc caactactgt    240
gacggagaat gttcgttccc taacgcgcac atgaacgcca ccaaccacgc catcgtgacc    300
ctggttcacc tcatgaaccc cgagtacgtc ccccgtgct gtgcgcccac gaaactcaac    360
gccatctcgc tctacttcga cgacaactcc aacgtcatcc tgaaatacag gaacatggtc    420
gtccgggcct gtggctgcca ctaggatccg taa                                 453

<210> SEQ ID NO 57
<211> LENGTH: 774
<212> TYPE: DNA
<213> ORGANISM: Rangifer tarandus

<400> SEQUENCE: 57
cggatctaca aggactgtgt tgtgggcagt tttaaaaacc aaactttttct tatcagcatt    60 taccaagtct tacaggagca tcagcacaga gactccgacc tgtttctgct gggcacgcgc    120
gccgtgtggg cctcagaggc gggctggctg gagttcgaca tcacggccac cagcaacctg    180
tgggtcctga ccccgcagca caacatgggg ctgcagctga gcgtggtcac gcgtgacggg    240
ctcagcatca gccccggggc tgcgggcctg gtgggcaggg acggcccta cgacaagcag    300 cccttcatgt ggcctttctt caaggccagc gaggcccacg tgcgcagcgc ccgctcggcc    360
cccgggcggc gccggcagca ggcccggaac cgctccaccc cggcccagga cgtgtcgcgg    420
gcctccagcg cctcagacta acagcagc gagctgaaaa cggcctgcag aaagcacgag    480
ctctacgtga gcttccagga cctggggtgg caggactgga tcattgcccc caagggctac    540
```

```
gctgccaact actgtgacgg agaatgttcg ttccctctca acgcgcacat gaacgccacc      600
aaccacgcca tcgtgcagac cctggttcac ctcatgaacc cgagtacgt ccccaagccg       660 tgctgtgcgc ccacgaaact caacgccatc tcggtgctct acttcgacga caactccaac     720
gtcatcctga aaagtacag gaacatggtc gtccgggcct gtggctgcca ctaa            774
```

```
<210> SEQ ID NO 58
<211> LENGTH: 504
<212> TYPE: DNA
<213> ORGANISM: Rangifer tarandus
<220> FEATURE:
<221> NAME/KEY: misc_feature
<222> LOCATION: (18)..(18)
<223> OTHER INFORMATION: n=g or c
<220> FEATURE:
<221> NAME/KEY: misc_feature
<222> LOCATION: (24)..(24)
<223> OTHER INFORMATION: n=c or g
<220> FEATURE:
<221> NAME/KEY: misc_feature
<222> LOCATION: (30)..(30)
<223> OTHER INFORMATION: n=c or g
<220> FEATURE:
<221> NAME/KEY: misc_feature
<222> LOCATION: (297)..(297)
<223> OTHER INFORMATION: n=g or c
<220> FEATURE:
<221> NAME/KEY: misc_feature
<222> LOCATION: (309)..(309)
<223> OTHER INFORMATION: n=g or c
<220> FEATURE:
<221> NAME/KEY: misc_feature
<222> LOCATION: (394)..(394)
<223> OTHER INFORMATION: n=c or a
<220> FEATURE:
<221> NAME/KEY: misc_feature
<222> LOCATION: (396)..(396)
<223> OTHER INFORMATION: n=c or g
<220> FEATURE:
<221> NAME/KEY: misc_feature
<222> LOCATION: (411)..(411)
<223> OTHER INFORMATION: n=c or g
<220> FEATURE:
<221> NAME/KEY: misc_feature
<222> LOCATION: (417)..(417)
<223> OTHER INFORMATION: n=c or t

<400> SEQUENCE: 58
atggatccgt cggccccngg gcgncgccgn cagcaggccc ggaaccgctc caccccggcc      60
caggacgtgt cgcgggcctc cagcgcctca gactacaaca gcagcgagct gaaaacggcc     120
tgcagaaagc acgagctcta cgtgagcttc caggacctgg ggtggcagga ctggatcatt     180
gcccccaagg gctacgctgc caactactgt gacggagaat gttcgttccc tctcaacgcg     240
cacatgaacg ccaccaacca cgccatcgtg cagaccctgg ttcacctcat gaacccngag    300
tacgtcccna agccgtgctg tgcgcccacg aaactcaacg ccatctcggt gctctacttc     360
gacgacaact ccaacgtcat cctgaaaaag tacngnaaca tggtcgtccg ngcctgnggc     420
tgccacaagc ttgggcccga acaaaaactc atctcagaag aggatctgaa tagcgccgtc     480
gaccatcatc atcatcatca ttga                                           504
```

```
<210> SEQ ID NO 59
<211> LENGTH: 167
<212> TYPE: PRT
<213> ORGANISM: Rangifer tarandus

<400> SEQUENCE: 59

Met Asp Pro Ser Ala Pro Gly Arg Arg Arg Gln Gln Ala Arg Asn Arg
1               5                   10                  15
```

```
Ser Thr Pro Ala Gln Asp Val Ser Arg Ala Ser Ser Ala Ser Asp Tyr
            20                  25                  30

Asn Ser Ser Glu Leu Lys Thr Ala Cys Arg Lys His Glu Leu Tyr Val
        35                  40                  45

Ser Phe Gln Asp Leu Gly Trp Gln Asp Trp Ile Ile Ala Pro Lys Gly
    50                  55                  60

Tyr Ala Ala Asn Tyr Cys Asp Gly Glu Cys Ser Phe Pro Leu Asn Ala
65                  70                  75                  80

His Met Asn Ala Thr Asn His Ala Ile Val Gln Thr Leu Val His Leu
                85                  90                  95

Met Asn Pro Glu Tyr Val Pro Lys Pro Cys Cys Ala Pro Thr Lys Leu
            100                 105                 110

Asn Ala Ile Ser Val Leu Tyr Phe Asp Asp Asn Ser Asn Val Ile Leu
        115                 120                 125

Lys Lys Tyr Arg Asn Met Val Val Arg Ala Cys Gly Cys His Lys Leu
    130                 135                 140

Gly Pro Glu Gln Lys Leu Ile Ser Glu Glu Asp Leu Asn Ser Ala Val
145                 150                 155                 160

Asp His His His His His His
                165

<210> SEQ ID NO 60
<211> LENGTH: 178
<212> TYPE: PRT
<213> ORGANISM: Rangifer tarandus

<400> SEQUENCE: 60

Met Asp Pro Gln Ala Lys His Lys Gln Arg Lys Arg Gly Thr Ser Ala
1               5                   10                  15

Pro Gly Arg Arg Arg Gln Gln Ala Arg Asn Arg Ser Thr Pro Ala Gln
            20                  25                  30

Asp Val Ser Arg Ala Ser Ser Ala Ser Asp Tyr Asn Ser Ser Glu Leu
        35                  40                  45

Lys Thr Ala Cys Arg Lys His Glu Leu Tyr Val Ser Phe Gln Asp Leu
    50                  55                  60

Gly Trp Gln Asp Trp Ile Ile Ala Pro Lys Gly Tyr Ala Ala Asn Tyr
65                  70                  75                  80

Cys Asp Gly Glu Cys Ser Phe Pro Leu Asn Ala His Met Asn Ala Thr
                85                  90                  95

Asn His Ala Ile Val Gln Thr Leu Val His Leu Met Asn Pro Glu Tyr
            100                 105                 110

Val Pro Lys Pro Cys Cys Ala Pro Thr Lys Leu Asn Ala Ile Ser Val
        115                 120                 125

Leu Tyr Phe Asp Asp Asn Ser Asn Val Ile Leu Lys Lys Tyr Arg Asn
    130                 135                 140

Met Val Val Arg Ala Cys Gly Cys His Lys Leu Gly Pro Glu Gln Lys
145                 150                 155                 160

Leu Ile Ser Glu Glu Asp Leu Asn Ser Ala Val Asp His His His His
                165                 170                 175

His His

<210> SEQ ID NO 61
<211> LENGTH: 537
<212> TYPE: DNA
<213> ORGANISM: Rangifer tarandus
<220> FEATURE:
```

```
<221> NAME/KEY: misc_feature
<222> LOCATION: (51)..(51)
<223> OTHER INFORMATION: n=g or c
<220> FEATURE:
<221> NAME/KEY: misc_feature
<222> LOCATION: (57)..(57)
<223> OTHER INFORMATION: n=c or g
<220> FEATURE:
<221> NAME/KEY: misc_feature
<222> LOCATION: (63)..(63)
<223> OTHER INFORMATION: n=c or g
<220> FEATURE:
<221> NAME/KEY: misc_feature
<222> LOCATION: (330)..(330)
<223> OTHER INFORMATION: n=g or c
<220> FEATURE:
<221> NAME/KEY: misc_feature
<222> LOCATION: (342)..(342)
<223> OTHER INFORMATION: n=g or c
<220> FEATURE:
<221> NAME/KEY: misc_feature
<222> LOCATION: (427)..(427)
<223> OTHER INFORMATION: n=c or a
<220> FEATURE:
<221> NAME/KEY: misc_feature
<222> LOCATION: (429)..(429)
<223> OTHER INFORMATION: n=c or g
<220> FEATURE:
<221> NAME/KEY: misc_feature
<222> LOCATION: (444)..(444)
<223> OTHER INFORMATION: n=c or g
<220> FEATURE:
<221> NAME/KEY: misc_feature
<222> LOCATION: (450)..(450)
<223> OTHER INFORMATION: n=c or t

<400> SEQUENCE: 61
atggatccgc aagcaaaaca taaacagcgc aaacgcggta cctcggcccc ngggcgncgc      60
cgncagcagg cccggaaccg ctccaccccg gcccaggacg tgtcgcgggc ctccagcgcc     120
tcagactaca acagcagcga gctgaaaacg gcctgcagaa agcacgagct ctacgtgagc     180
ttccaggacc tggggtggca ggactggatc attgccccca agggctacgc tgccaactac     240
tgtgacggag aatgttcgtt ccctctcaac gcgcacatga acgccaccaa ccacgccatc     300
gtgcagaccc tggttcacct catgaacccn gagtacgtcc cnaagccgtg ctgtgcgccc     360
acgaaactca cgccatctc ggtgctctac ttcgacgaca actccaacgt catcctgaaa      420
aagtacngna acatggtcgt ccgngcctgn ggctgccaca agcttgggcc cgaacaaaaa     480
ctcatctcag aagaggatct gaatagcgcc gtcgaccatc atcatcatca tcattga       537

<210> SEQ ID NO 62
<211> LENGTH: 183
<212> TYPE: PRT
<213> ORGANISM: Rangifer tarandus

<400> SEQUENCE: 62

Met Lys Tyr Leu Leu Pro Thr Ala Ala Gly Leu Leu Leu Ala
1               5                   10                  15

Ala Gln Pro Ala Met Ala Met Asp Ile Gly Ile Asn Ser Asp Pro Ser
                20                  25                  30

Ala Pro Gly Arg Arg Arg Gln Gln Ala Arg Asn Arg Ser Thr Pro Ala
            35                  40                  45

Gln Asp Val Ser Arg Ala Ser Ser Ala Ser Asp Tyr Asn Ser Ser Glu
        50                  55                  60

Leu Lys Thr Ala Cys Arg Lys His Glu Leu Tyr Val Ser Phe Gln Asp
65                  70                  75                  80

Leu Gly Trp Gln Asp Trp Ile Ile Ala Pro Lys Gly Tyr Ala Ala Asn
```

```
                        85                  90                  95
Tyr Cys Asp Gly Glu Cys Ser Phe Pro Leu Asn Ala His Met Asn Ala
                100                 105                 110

Thr Asn His Ala Ile Val Gln Thr Leu Val His Leu Met Asn Pro Glu
        115                 120                 125

Tyr Val Pro Lys Pro Cys Cys Ala Pro Thr Lys Leu Asn Ala Ile Ser
130                 135                 140

Val Leu Tyr Phe Asp Asp Asn Ser Asn Val Ile Leu Lys Lys Tyr Arg
145                 150                 155                 160

Asn Met Val Val Arg Ala Cys Gly Cys His Lys Leu Ala Ala Ala Leu
                165                 170                 175

Glu His His His His His His
        180

<210> SEQ ID NO 63
<211> LENGTH: 552
<212> TYPE: DNA
<213> ORGANISM: Rangifer tarandus
<220> FEATURE:
<221> NAME/KEY: misc_feature
<222> LOCATION: (102)..(102)
<223> OTHER INFORMATION: n=g or c
<220> FEATURE:
<221> NAME/KEY: misc_feature
<222> LOCATION: (108)..(108)
<223> OTHER INFORMATION: n=c or g
<220> FEATURE:
<221> NAME/KEY: misc_feature
<222> LOCATION: (114)..(114)
<223> OTHER INFORMATION: n=c or g
<220> FEATURE:
<221> NAME/KEY: misc_feature
<222> LOCATION: (381)..(381)
<223> OTHER INFORMATION: n=g or c
<220> FEATURE:
<221> NAME/KEY: misc_feature
<222> LOCATION: (393)..(393)
<223> OTHER INFORMATION: n=g or c
<220> FEATURE:
<221> NAME/KEY: misc_feature
<222> LOCATION: (478)..(478)
<223> OTHER INFORMATION: n=c or a
<220> FEATURE:
<221> NAME/KEY: misc_feature
<222> LOCATION: (480)..(480)
<223> OTHER INFORMATION: n=c or g
<220> FEATURE:
<221> NAME/KEY: misc_feature
<222> LOCATION: (495)..(495)
<223> OTHER INFORMATION: n=c or g
<220> FEATURE:
<221> NAME/KEY: misc_feature
<222> LOCATION: (501)..(501)
<223> OTHER INFORMATION: n=c or t

<400> SEQUENCE: 63
atgaaatacc tgctgccgac cgctgctgct ggtctgctgc tcctcgctgc ccagccggcg      60
atggccatgg atatcggaat taattcggat ccgtcggccc cngggcgncg ccgncagcag     120
gcccggaacc gctccacccc ggcccaggac gtgtcgcggg cctccagcgc ctcagactac     180
aacagcagcg agctgaaaac ggcctgcaga agcacgagc tctacgtgag cttccaggac      240
ctggggtggc aggactggat cattgccccc aagggctacg ctgccaacta ctgtgacgga     300
gaatgttcgt tccctctcaa cgcgcacatg aacgccacca accacgccat cgtgcagacc     360
ctggttcacc tcatgaaccc ngagtacgtc ccnaagccgt gctgtgcgcc cacgaaactc     420
aacgccatct cggtgctcta cttcgacgac aactccaacg tcatcctgaa aaagtacngn     480
```

```
aacatggtcg tccgngcctg nggctgccac aagcttgcgg ccgcactcga gcaccaccac    540
caccaccact ga                                                        552
```

<210> SEQ ID NO 64
<211> LENGTH: 194
<212> TYPE: PRT
<213> ORGANISM: Rangifer tarandus

<400> SEQUENCE: 64

Met Lys Tyr Leu Leu Pro Thr Ala Ala Gly Leu Leu Leu Leu Ala
1               5                   10                  15

Ala Gln Pro Ala Met Ala Met Asp Ile Gly Ile Asn Ser Asp Pro Gln
            20                  25                  30

Ala Lys His Lys Gln Arg Lys Arg Gly Thr Ser Ala Pro Gly Arg Arg
        35                  40                  45

Arg Gln Gln Ala Arg Asn Arg Ser Thr Pro Ala Gln Asp Val Ser Arg
    50                  55                  60

Ala Ser Ser Ala Ser Asp Tyr Asn Ser Ser Glu Leu Lys Thr Ala Cys
65                  70                  75                  80

Arg Lys His Glu Leu Tyr Val Ser Phe Gln Asp Leu Gly Trp Gln Asp
                85                  90                  95

Trp Ile Ile Ala Pro Lys Gly Tyr Ala Ala Asn Tyr Cys Asp Gly Glu
            100                 105                 110

Cys Ser Phe Pro Leu Asn Ala His Met Asn Ala Thr Asn His Ala Ile
        115                 120                 125

Val Gln Thr Leu Val His Leu Met Asn Pro Glu Tyr Val Pro Lys Pro
    130                 135                 140

Cys Cys Ala Pro Thr Lys Leu Asn Ala Ile Ser Val Leu Tyr Phe Asp
145                 150                 155                 160

Asp Asn Ser Asn Val Ile Leu Lys Lys Tyr Arg Asn Met Val Val Arg
                165                 170                 175

Ala Cys Gly Cys His Lys Leu Ala Ala Ala Leu Glu His His His His
            180                 185                 190

His His

<210> SEQ ID NO 65
<211> LENGTH: 585
<212> TYPE: DNA
<213> ORGANISM: Rangifer tarandus
<220> FEATURE:
<221> NAME/KEY: misc_feature
<222> LOCATION: (135)..(135)
<223> OTHER INFORMATION: n=g or c
<220> FEATURE:
<221> NAME/KEY: misc_feature
<222> LOCATION: (141)..(141)
<223> OTHER INFORMATION: n=c or g
<220> FEATURE:
<221> NAME/KEY: misc_feature
<222> LOCATION: (147)..(147)
<223> OTHER INFORMATION: n=c or g
<220> FEATURE:
<221> NAME/KEY: misc_feature
<222> LOCATION: (414)..(414)
<223> OTHER INFORMATION: n=g or c
<220> FEATURE:
<221> NAME/KEY: misc_feature
<222> LOCATION: (426)..(426)
<223> OTHER INFORMATION: n=g or c
<220> FEATURE:
<221> NAME/KEY: misc_feature
<222> LOCATION: (511)..(511)
<223> OTHER INFORMATION: n=c or a
<220> FEATURE:

```
<221> NAME/KEY: misc_feature
<222> LOCATION: (513)..(513)
<223> OTHER INFORMATION: n=c or g
<220> FEATURE:
<221> NAME/KEY: misc_feature
<222> LOCATION: (528)..(528)
<223> OTHER INFORMATION: n=c or g
<220> FEATURE:
<221> NAME/KEY: misc_feature
<222> LOCATION: (534)..(534)
<223> OTHER INFORMATION: n=c or t

<400> SEQUENCE: 65
```

| | | | | | |
|---|---|---|---|---|---|
| atgaaatacc | tgctgccgac | cgctgctgct | ggtctgctgc | tcctcgctgc | ccagccggcg | 60 |
| atggccatgg | atatcggaat | taattcggat | ccgcaagcaa | acataaaca | gcgcaaacgc | 120 |
| ggtacctcgg | ccccngggcg | ncgccgncag | caggcccgga | accgctccac | cccggcccag | 180 |
| gacgtgtcgc | gggcctccag | cgcctcagac | tacaacagca | gcgagctgaa | aacggcctgc | 240 |
| agaaagcacg | agtctctacgt | gagcttccag | gacctggggt | ggcaggactg | gatcattgcc | 300 |
| cccaagggct | acgctgccaa | ctactgtgac | ggagaatgtt | cgttccctct | caacgcgcac | 360 |
| atgaacgcca | ccaaccacgc | catcgtgcag | accctggttc | acctcatgaa | cccngagtac | 420 |
| gtcccnaagc | cgtgctgtgc | gcccacgaaa | ctcaacgcca | tctcggtgct | ctacttcgac | 480 |
| gacaactcca | acgtcatcct | gaaaaagtac | ngnaacatgg | tcgtccgngc | ctgnggctgc | 540 |
| cacaagcttg | cggccgcact | cgagcaccac | caccaccacc | actga | | 585 |

```
<210> SEQ ID NO 66
<211> LENGTH: 149
<212> TYPE: PRT
<213> ORGANISM: Rangifer tarandus

<400> SEQUENCE: 66
```

| Met | Ser | Gly | Ser | His | His | His | His | His | His | Ser | Ser | Gly | Ile | Glu | Gly |
|---|---|---|---|---|---|---|---|---|---|---|---|---|---|---|---|
| 1 | | | | 5 | | | | | 10 | | | | | 15 | |

| Arg | Gly | Ser | Ala | Pro | Gly | Arg | Arg | Gln | Gln | Arg | Asn | Arg | Ser | Thr |
|---|---|---|---|---|---|---|---|---|---|---|---|---|---|---|
| | | 20 | | | | | 25 | | | | | 30 | | |

| Pro | Ala | Gln | Asp | Val | Ser | Arg | Ser | Ser | Ala | Ser | Asp | Tyr | Asn | Ser | Ser |
|---|---|---|---|---|---|---|---|---|---|---|---|---|---|---|---|
| | | | 35 | | | | | 40 | | | | | 45 | | |

| Glu | Leu | Lys | Ala | Cys | Arg | Lys | His | Glu | Leu | Tyr | Val | Ser | Phe | Gln | Leu |
|---|---|---|---|---|---|---|---|---|---|---|---|---|---|---|---|
| | 50 | | | | | 55 | | | | | 60 | | | | |

| Gly | Trp | Gln | Asp | Trp | Ile | Ile | Ala | Pro | Lys | Gly | Ala | Ala | Asn | Tyr | Cys |
|---|---|---|---|---|---|---|---|---|---|---|---|---|---|---|---|
| 65 | | | | | 70 | | | | | 75 | | | | | 80 |

| Asp | Gly | Glu | Cys | Ser | Phe | Pro | Asn | Ala | His | Met | Asn | Ala | Thr | Asn | His |
|---|---|---|---|---|---|---|---|---|---|---|---|---|---|---|---|
| | | | | 85 | | | | | 90 | | | | | 95 | |

| Ala | Ile | Val | Thr | Leu | Val | His | Leu | Met | Asn | Pro | Glu | Tyr | Val | Pro | Pro |
|---|---|---|---|---|---|---|---|---|---|---|---|---|---|---|---|
| | | | 100 | | | | | 105 | | | | | 110 | | |

| Cys | Cys | Ala | Pro | Thr | Lys | Leu | Asn | Ala | Ile | Ser | Leu | Tyr | Phe | Asp | Asp |
|---|---|---|---|---|---|---|---|---|---|---|---|---|---|---|---|
| | | 115 | | | | | 120 | | | | | 125 | | | |

| Asn | Ser | Asn | Val | Ile | Leu | Lys | Tyr | Arg | Asn | Met | Val | Val | Arg | Ala | Cys |
|---|---|---|---|---|---|---|---|---|---|---|---|---|---|---|---|
| | 130 | | | | | 135 | | | | | 140 | | | | |

| Gly | Cys | His | Asp | Pro |
|---|---|---|---|---|
| 145 | | | | |

```
<210> SEQ ID NO 67
<211> LENGTH: 453
<212> TYPE: DNA
<213> ORGANISM: Rangifer tarandus

<400> SEQUENCE: 67
```

```
atgtctggtt ctcatcatca tcatcatcat agcagcggca tcgaaggccg cggctcggcc    60
cccgggcggc gccggcagca gcggaaccgc tccaccccgg cccaggacgt gtcgcggtcc   120
agcgcctcag actacaacag cagcgagctg aaagcctgca gaaagcacga gctctacgtg   180
agcttccagc tggggtggca ggactggatc attgccccca agggcgctgc caactactgt   240
gacggagaat gttcgttccc taacgcgcac atgaacgcca ccaaccacgc catcgtgacc   300
ctggttcacc tcatgaaccc cgagtacgtc ccccgtgct gtgcgcccac gaaactcaac   360
gccatctcgc tctacttcga cgacaactcc aacgtcatcc tgaaatacag gaacatggtc   420
gtccgggcct gtggctgcca ctaggatccg taa                                453
```

<210> SEQ ID NO 68
<211> LENGTH: 257
<212> TYPE: PRT
<213> ORGANISM: Rangifer tarandus

<400> SEQUENCE: 68

```
Arg Ile Tyr Lys Asp Cys Val Val Gly Ser Phe Lys Asn Gln Thr Phe
1               5                   10                  15

Leu Ile Ser Ile Tyr Gln Val Leu Gln Glu His Gln His Arg Asp Ser
            20                  25                  30

Asp Leu Phe Leu Leu Gly Thr Arg Ala Val Trp Ala Ser Glu Ala Gly
        35                  40                  45

Trp Leu Glu Phe Asp Ile Thr Ala Thr Ser Asn Leu Trp Val Leu Thr
    50                  55                  60

Pro Gln His Asn Met Gly Leu Gln Leu Ser Val Val Thr Arg Asp Gly
65                  70                  75                  80

Leu Ser Ile Ser Pro Gly Ala Ala Gly Leu Val Gly Arg Asp Gly Pro
                85                  90                  95

Tyr Asp Lys Gln Pro Phe Met Val Ala Phe Phe Lys Ala Ser Glu Ala
            100                 105                 110

His Val Arg Ser Ala Arg Ser Ala Pro Gly Arg Arg Gln Gln Ala
        115                 120                 125

Arg Asn Arg Ser Thr Pro Ala Gln Asp Val Ser Arg Ala Ser Ser Ala
    130                 135                 140

Ser Asp Tyr Asp Ser Ser Glu Leu Lys Thr Ala Cys Arg Lys His Glu
145                 150                 155                 160

Leu Tyr Val Ser Phe Gln Asp Leu Gly Trp Gln Asp Trp Ile Ile Ala
                165                 170                 175

Pro Lys Gly Tyr Ala Ala Asn Tyr Cys Asp Gly Glu Cys Ser Phe Pro
            180                 185                 190

Leu Asn Ala His Met Asn Ala Thr Asn His Ala Ile Val Gln Thr Leu
        195                 200                 205

Val His Leu Met Asn Pro Glu Tyr Val Pro Lys Pro Cys Cys Ala Pro
    210                 215                 220

Thr Lys Leu Asn Ala Ile Ser Val Leu Tyr Phe Asp Asp Asn Ser Asp
225                 230                 235                 240

Val Ile Leu Lys Lys Tyr Arg Asn Met Val Val Arg Ala Cys Gly Cys
                245                 250                 255

His
```

<210> SEQ ID NO 69
<211> LENGTH: 774
<212> TYPE: DNA
<213> ORGANISM: Rangifer tarandus -continued

```
<400> SEQUENCE: 69
cggatctaca aggactgtgt tgtgggcagt tttaaaaacc aaacttttct tatcagcatt        60
taccaagtct tacaggagca tcagcacaga gactccgacc tgtttctgct gggcacgcgc       120
gccgtgtggg cctcagaggc gggctggctg gagttcgaca tcacggccac cagcaacctg       180
tgggtcctga ccccgcagca caacatgggg ctgcagctga gcgtggtcac gcgtgacggg       240
ctcagcatca gccccgggc tgcgggcctg gtgggcaggg acggcccta cgacaagcag         300 cccttcatgg tggccttctt caaggccagc gaggcccacg tgcgcagcgc ccgctcggcc       360
cccgggcggc gccggcagca ggcccggaac cgctccaccc cggcccagga cgtgtcgcgg       420
gcctccagcg cctcagacta caacagcagc gagctgaaaa cggcctgcag aaagcacgag       480
ctctacgtga gcttccagga cctggggtgg caggactgga tcattgcccc caagggctac       540
gctgccaact actgtgacgg agaatgttcg ttccctctca acgcgcacat gaacgccacc       600
aaccacgcca tcgtgcagac cctggttcac ctcatgaacc ccgagtacgt ccccaagccg       660
tgctgtgcgc ccacgaaact caacgccatc tcggtgctct acttcgacga caactccaac       720
gtcatcctga aaaagtacag gaacatggtc gtccgggcct gtggctgcca ctaa            774
```

BONE MORPHOGENETIC PROTEINS CONTAINING A HEPARIN BINDING SITE AND OSTEOGENIC DEVICES AND PHARMACEUTICAL PRODUCTS CONTAINING THEREOF

FIELD OF THE INVENTION

The present invention relates to bone formation inducing proteins called bone morphogenetic proteins (BMP), especially BMP-6, containing a heparin binding site, nucleic acid molecules encoding said proteins, vectors containing said nucleic acid molecules and host cells expressing said proteins. The present invention relates also to the use of said bone morphogenetic proteins for treating disorders, such as disorders related to bone and cartilage formation. The present invention further relates to osteogenic devices and pharmaceutical compositions containing said proteins.

BACKGROUND OF THE INVENTION

The phenomenon of osteoinduction was recognized by Lancroix in 1945 when he demonstrated that acid alcohol bone extracts induced heterotopic bone formation in ectopic sites. Twenty years later Urist and his co-workers decalcified bone matrix and observed new cartilage and bone formation when implanted intramuscularly. These discoveries led to isolation and purification of bone inducing agent named BMPs from bone matrix of different species and years later to cloning and characterization of several cDNAs encoding these novel proteins. The biological activity of BMPs has been determined by bioassay in rat or mouse muscle bounces or by ALP measurements in mammalian cell cultures.

Previous studies since 1965 have shown that BMPs are part of the TGF-β superfamily and like all the family members they have multiple effects on cell migration, growth and differentiation especially in bone formation and tissue repair but also in embryogenesis or cancer. They are low molecular weight hydrophobic glycoproteins which are soluble to chaotrophic agents such as urea and guanidinium hydrochloride but are resistant to several proteases, for example collagenases.

BMPs are produced as large precursor molecules which are processed proteolytically to mature peptides after the translation. Like all the members of TGF-β superfamily, BMPs have the pattern of seven cysteine residues in their C-terminal mature region. Between these cysteines there are three disulfide bonds within mature BMP monomers and one disulfide bond which combines two monomers into a biologically active BMP dimer.

BMPs act through specific transmembrane receptors located on cell surface of the target cells. The BMP receptors are serin-threonin kinases which resemble TGF-β receptors and are divided into two subgroups: type I and type II receptors. BMPs can bind strongly only to the heterotetrameric complex of these receptors. This complex formation is essential to the BMP signal transduction. Inside the target cell, BMP signals are transmitted to the nucleus via specific signal molecules called Smads, which are also responsible for suppression of BMP signals.

Until now, 16 different BMPs have been characterized and seven of them (BMPs 2-7 and 9) have shown to be able to induce bone formation when implanted in ectopic sites. According to the amino acid sequence of the mature part these BMPs are divided into two subgroups. BMPs 2 and 4 are 86% identical and BMPs 5, 6 and 7 are 78% identical. Between these two groups the identity is only about 56%. The amino acid sequence of BMP-3 is about 45% alike with BMPs 2 and 4 and BMP-9 is 50-55% identical with BMPs 2, 4, 5, 6 and 7. Due to high homology and small variety in size, BMPs are quite difficult, very time consuming and expensive to separate, purify and identify from each other at protein level. This is the reason why most of the BMPs are nowadays being produced using molecular biological tools. Different kinds of recombinant protein techniques have been tested and both eukaryotic and prokaryotic systems have been utilized.

Majority of research has focused on human recombinant BMPs, but with regard to effective bone induction antlers of Cervidae family form an interesting research area. Antlers are bony cranial organs typical to the Cervidae family and they differ from Bovidae horns in their growing pattern. Antlers grow from the tip and males cast them away once per year. It has been suggested that antlers are the fastest growing structures through the mammalian species and they are known to be the only structures that regenerate completely every year. Antlers are formed by modified endochondral ossification meaning that the process is performed through the highly vascularized cartilage model which is calcified and finally transformed into bone. Antlers form an interesting model of adult regenerating mineralized tissue, and bone remodeling has been shown to continue until the time of antler casting. Although the ultimate reason for the amazing speed of antler growth has not yet been resolved, antlers have been shown to contain several BMPs. Deer antler has been proven to express BMP-2 and BMP-4 (Feng et al 1997 Biochim Biophys Acta 1350:47-52; Feng et al. 1995 Biochim Biophys Acta 1263: 163-168). In addition, reindeer antlers express BMP-3b (Kapanen et al 2002 J Biomed Mat Res 59:78-83). Yet, it is also possible that there is one or more totally uncovered factor(s) which are responsible for antler growth speed.

Due to their osteoinductive capacity, both BMPs extracted from demineralized bone matrix and BMPs produced by recombinant technique are very interesting and highly potential alternatives to bone grafting. Different BMPs have been used in many experimental and clinical studies.

Bone morphogenetic protein 6 has been characterized from many different origins including some mammalian species like mouse, rat, human and bovine. Yet, it has not been characterized from deer animals unlike BMP-2, BMP-3b and BMP-4 which all have been cloned from antlers of either deer or reindeer, both members of Cervidae family (Feng et al 1997; Feng et al 1995; Kapanen et al 2002). Considering the fact that BMP-6 is an important regulator molecule in chondrogenesis it is probable that it is expressed in antlers just as the earlier cloned members of BMP family.

Until now, BMP-3b has been the only BMP characterized in reindeer antler tissue (Kapanen et al 2002).

U.S. Pat. No. 5,399,677 discloses DNA molecules encoding mutant forms of bone morphogenetic proteins. The mutant forms of BMP can be produced bacterially and refolded to produce biologically active homodimers or heterodimers of BMP. A method of making such mutant BMP is also disclosed. Said mutant forms are useful since they are correctly folded when produced in bacterial hosts.

WO 98/51354 discloses osteogenic devices and methods of use thereof for repair of bone and cartilage defects. The method for producing new bone growth at bone defect site in a mammal comprises the step of implanting in a defect site a calcium phosphate matrix comprising at least one osteogenic protein. Said osteogenic proteins include several morphogens, such as bone morphogenetic proteins.

U.S. Pat. No. 6,207,813 discloses purified human BMP-6 proteins and processes for producing them. The publication also discloses commonly known pharmaceutical compositions, medical uses and methods employing said human BMP-6 protein. BMP-6 has been localized in hypertrophic cartilage and it is an important regulator in chondrocyte maturation process. When mouse BMP-6 overexpressing CHO cells were introduced directly into the subcutaneous tissue of athymic nude mice, they formed tumors surrounded by extensive connective tissue containing large regions of cartilage and bone. This suggests that BMP-6 induces endochondral bone formation in vivo. BMP-6 has also been indicated to enhance osteoblastic differentiation of pluripotent mesenchymal progenitor cells in vitro when the cells were transfected with vector overexpressing mouse BMP-6. Furthermore, recombinant human BMP-6 has been shown to take part in osteoblastic differentiation of bone marrow stromal cells in vitro. The osteoinductive activity of recombinant human BMP-6 produced in CHO cells has been verified by in vivo test in rat muscle. Nevertheless, the biological activity of BMP-6 from any origin produced as recombinant protein in E. coli system has not yet been published. Neither has anybody published information of the biological activity of BMP-6 cloned from the antler tissue of any member of Cervidae family.

EP 1131087 discloses further use for morphogenetic proteins, such as BMP proteins. It is shown that exposing cancer cells to morphogens inhibits cancer cell growth and causes such cells to differentiate away from the cancerous phenotype. The use of morphogen can influence cancer cell fate and, in turn, alleviate the symptoms of cancer. Preferred morphogens disclosed include BMP-6.

WO 90/11366 discloses BMP proteins including a bovine BMP-6 for which DNA and amino acid sequences are presented. The amino acid sequence does not correspond to the one currently known for bovine BMP-6 but instead it is identical to the reindeer BMP-6 disclosed herein. The activity or other properties of said BMP-6 are not tested or described in WO 90/11366.

Although some applications of known BMP proteins as bone and cartilage forming inducers or for alleviating the symptoms of cancer are already known, there is still need for better methods for isolating such proteins and for better morphogenetic proteins, for example ones which possess more efficient bone forming properties or are more soluble. Such proteins would be useful for better therapeutic methods and applications. Also methods for producing such proteins would be useful.

SUMMARY OF THE INVENTION

The present invention relates to an isolated bone morphogenetic protein (BMP), which is not BMP-2, containing a heparin binding site (HBS). The heparin binding site improves the expression of the recombinant BMP protein and also enhances the biological activity thereof. Further, the heparin binding site significantly helps the expression of recombinant bone morphogenetic proteins in bacterial cells, such as E. coli.

In the present invention a BMP-6 protein isolated from reindeer, despite having high sequence homology with already known bone morphogenetic proteins, has very advantageous properties related to bone and cartilage forming. Said properties are substantially better than the properties of the known corresponding BMP proteins. Said bone morphogenetic protein of the present invention and homologues thereof are useful for inducing bone and cartilage formation in several kinds of applications, such as therapeutic applications. The isolated bone morphogenetic protein may include also the propeptide part of the protein. The presence of this part stabilizes the BMP and modulate its functional activity.

Further, the cDNA of the BMP-6 protein of the present invention was truncated without causing any changes in protein sequence to get as high expression levels as possible when produced as recombinant protein in a host cell system. A heparin binding site (HBS) was added in front of the rdBMP-6 gene and this addition made the expression possible also in E. coli TOP10 strain where the expression of plain rdBMP-6 was blocked.

One aspect of the present invention relates to an isolated bone morphogenetic protein containing the essential amino acids of amino acid sequence of SEQ ID NO: 1.

Another aspect of the present invention relates to said isolated bone morphogenetic protein further containing a BMP propeptide.

Another aspect of the present invention relates to an isolated DNA molecule encoding said bone morphogenetic proteins.

Still another aspect of the present invention relates to a nucleic acid vector containing said isolated DNA molecule.

Still another aspect of the present invention relates to a recombinant host cell containing said DNA molecule or the nucleic acid vector mentioned above.

Still another aspect of the present invention relates to bone morphogenetic protein which is produced by culturing said recombinant host cell to express said bone morphogenetic protein and by recovering said bone morphogenetic protein from said host cell.

Still another aspect of the present invention relates to a recombinant host cell expressing said bone morphogenetic protein.

Still another aspect of the present invention relates to a pharmaceutical composition containing said bone morphogenetic protein.

Still another aspect of the present invention relates to said isolated bone morphogenetic protein for use as medicament.

Still another aspect of the present invention relates to the use of said isolated bone morphogenetic protein for manufacturing medicament for disorders related to bone or cartilage defects wherein regeneration, repair or growth thereof is desired, or other diseases, such as cancer.

Still another aspect of the present invention relates to an osteogenic device for treating said disorders said device containing said isolated bone morphogenetic protein.

Still another aspect of the present invention relates to a method for inducing the formation of cartilage and/or bone by treating said cartilage and/or bone with said isolated bone morphogenetic protein.

Still another aspect of the present invention relates to a method for treating said disorders related to bone or cartilage defects wherein regeneration, repair or growth thereof is desired, or other diseases, such as cancer, by administering said isolated bone morphogenetic protein to a patient suffering from said disorders.

Still another aspect of the present invention relates to a method for improving the expression of a recombinant BMP protein in a bacterial host by adding a heparin binding site to the amino terminus of said protein to be expressed.

Still another aspect of the present invention relates to a method for improving or enhancing the biological activity of a recombinant BMP protein by adding a heparin binding site to the amino terminus of said protein.

Still another aspect of the present invention relates to a method for expressing a BMP protein in a bacterial host, such as E. coli, by adding a heparin binding site to the amino terminus of said protein wherein the protein shows lowered immunogenicity when compared to a BMP expressed in for example yeast host.

BRIEF DESCRIPTION OF THE DRAWINGS

FIG. 5 shows amino acid (SEQ ID NO: 58) and nucleotide sequences (SEQ ID NO: 59) of reindeer BMP-6 mature part expressed from pMU20 and pMU90. Mature part of reindeer BMP-6 is boxed and mutated nucleotide codons are shown in separate boxes with changed nucleotides marked by bold letters. Cysteine residues typical for TGF-β superfamily are also marked by bold letters.

FIG. 6 shows amino acid (SEQ ID NO: 60) and nucleotide sequences (SEQ ID NO: 61) of reindeer BMP-6 mature part with heparin binding site (HBS) expressed from pTrcHBSrd6A and pTrcHBSrd6. Heparin binding site is marked by bold italic letters. Mature part of reindeer BMP-6 is boxed and mutated nucleotide codons are shown in separate boxes with changed nucleotides marked by bold letters. Cysteine residues typical for TGF-β superfamily are also marked by bold letters.

FIG. 7 shows amino acid (SEQ ID NO: 62) and nucleotide sequences (SEQ ID NO: 63) of reindeer BMP-6 mature part expressed from pETrd6A and pETrd6. Mature part of reindeer BMP-6 is boxed and mutated nucleotide codons are shown in separate boxes with changed nucleotides marked by bold letters. Cysteine residues typical for TGF-β superfamily are also marked by bold letters.

FIG. 8 shows amino acid (SEQ ID NO: 64) and nucleotide sequences (SEQ ID NO: 65) of reindeer BMP-6 mature part with heparin binding site (HBS) expressed from pTrcETrd6A and pTrcETrd6. Heparin binding site is marked by bold italic letters. Mature part of reindeer BMP-6 is boxed and mutated nucleotide codons are shown in separate boxes with changed nucleotides marked by bold letters. Cysteine residues typical for TGF-β superfamily are also marked by bold letters.

FIG. 9 shows amino acid (SEQ ID NO: 66) and nucleotide sequence (SEQ ID NO: 67) of recombinant reindeer BMP-6 mature part expressed from pMU200 plasmid. Mature part of reindeer BMP-6 is boxed. Cysteine residues typical for TGF-β superfamily are also marked by bold letters.

FIGS. 10 A and B (continued) show partial amino acid (SEQ ID NO: 68) and nucleotide sequence (SEQ ID NO: 69) of reindeer BMP-6. Mature part is boxed and cysteines typical for TGF-β superfamily members are marked with bold letters. Amino acids 1-118 before the mature part represent the BMP propeptide.

DETAILED DESCRIPTION OF THE INVENTION

Figure 1:
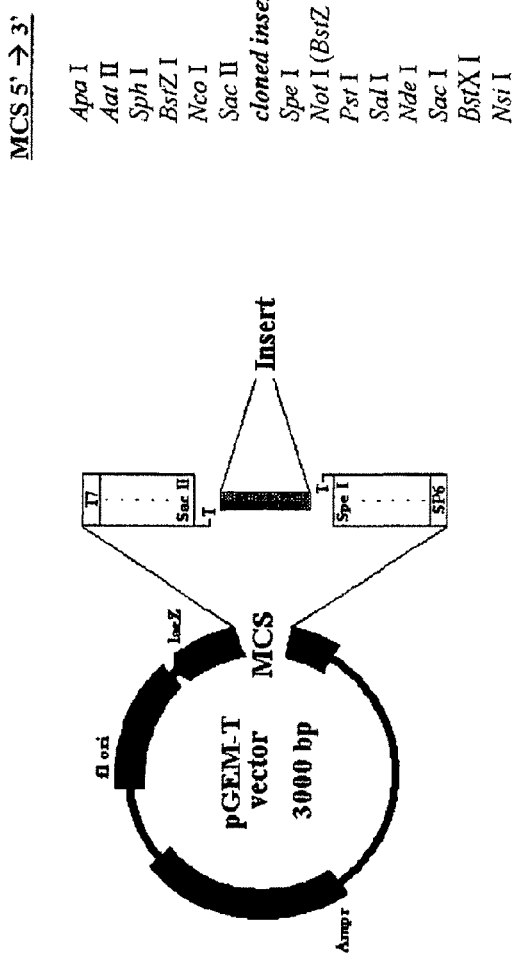
FIG. 1 shows plasmids containing various inserts in PCR vector pGEM-T® (Promega).

The present invention provides a bone morphogenetic protein with a heparin binding site (HBS). Generally this is an amino acid sequence capable of binding heparin. In one embodiment said heparin binding site is located at the amino terminus of said BMP, such as before the sequence of SEQ ID NO: 1 or functional homologue thereof. In one embodiment the heparin binding site contains amino acid sequence AKHKQRKRGT (SEQ ID NO: 5) (FIG. 8) or QAKHKQRKRGT (SEQ ID NO: 6) (FIG. 6). Said heparin binding site may also be a functional homologue, derivative or fragment thereof.

The bone morphogenetic proteins useful in the present invention comprise all the known bone morphogenetic proteins excluding BMP-2. Preferred bone morphogenetic proteins are selected from BMP3 (such as BMP-3c), BMP-4 and BMP-6 and homologues thereof. More preferably said proteins are originated from reindeer. References are made to the patent applications FI20055256 and FI20055258 disclosing reindeer BMP-3c (SEQ ID NO: 3) and BMP-4 (SEQ ID NO: 4), respectively, by the present inventors and from which the present application claims priority. These and all the other documents referred herein are incorporated by reference. All said BMPs originated from reindeer have shown to have especially good bone and cartilage forming properties. The reindeer BMP-6 protein is described herein in details.

The highest homology at amino acid level among mature parts of previously known BMP-6 is between mouse and rat (98%) and between rat and human (98%) (Table 1). Cloning and characterization of reindeer BMP-6 mature part revealed that it has the highest homology with bovine BMP-6 (Wozney et al 1998). At the amino acid level there was difference of only one amino acid between these two polypeptides, and homology reached 99% (Table 1). Even at the nucleotide level the homology between mature parts of reindeer and bovine BMP-6 was 95%, which is as high as between those of mouse and rat (Table 1). Generally BMP-6 has homology also with other types of BMPs, for example with BMP-5 and BMP-7.

TABLE 1

Homology of BMP-6 mature part of different mammalian origin at nucleotide and amino acid level presented as percentages (%)

| Origin | Reindeer | | Bovine | | Human | | Mouse | | Rat | |
| --- | --- | --- | --- | --- | --- | --- | --- | --- | --- | --- |
| | nt | aa | nt | aa | nt | aa | nt | aa | nt | aa |
| Reindeer | 100 | 100 | 95 | 99 | 84 | 95 | 84 | 93 | 84 | 95 |
| Bovine | 95 | 99 | 100 | 100 | 84 | 94 | 85 | 92 | 85 | 92 |
| Human | 84 | 95 | 84 | 94 | 100 | 100 | 88 | 96 | 88 | 98 |
| Mouse | 84 | 93 | 85 | 92 | 88 | 96 | 100 | 100 | 95 | 98 |
| Rat | 84 | 95 | 85 | 94 | 88 | 98 | 95 | 98 | 100 | 100 |

(nt = nucleotides, aa = amino acids)

The following alignment shows the amino acid sequences of human and reindeer mature BMP-6 proteins (made with ClustalX 1.8 program (Thompson, J. D., Hig-gins, D. G. and Gibson, T. J. (1994) Nucleic Acids Research, 22: 4673-4680), rdBMP-6=reindeer BMP-6, hBMP-6=human BMP-6, the asterisks show the identical amino acids). The mature parts of these amino acid sequences differ by seven amino acids near the amino terminus. Probably the most essential differences are caused by the pralines in rdBMP-6, Pro3 and especially Pro16, which are very likely to affect the folding or structure of the mature protein. Human BMP-6 is the closest counterpart of reindeer BMP-6 having the activity thereof determined.

```
rdBMP-6   SAPGRRRQQARNRSTPAQDVSRASSASDYNSSELKTACRKHELYVSFQDLGWQDWIIAPK
hBMP-6    SASSRRRQQSRNRSTQSQDVARVSSASDYNSSELKTACRKHELYVSFQDLGWQDWIIAPK
          ..*.*.:*:*.************************************* rdBMP-6   GYAANYCDGECSFPLNAHMNATNHAIVQTLVHLMNPEYVPKPCCAPTKLNAISVLYFDDN
hBMP-6    GYAANYCDGECSFPLNAHMNATNHAIVQTLVHLMNPEYVPKPCCAPTKLNAISVLYFDDN
          ************************************************************ rdBMP-6   SNVILKKYRNMVVRACGCH (SEQ ID NO: 1)

hBMP-6    SNVILKKYRNMVVRACGCH (SEQ ID NO: 7)
          *******************
```

The "BMP-6 protein of the invention" or "bone morphogenetic protein of the invention" refer to a protein having bone morphogenetic (or morphogenic as both words are used interchangeably) activity, such as BMP-6 isolated from reindeer as described herein (SEQ ID NO: 1 of the attached sequence listing or rdBMP-6 in the alignment above), and includes homologues, analogs, derivatives and fragments thereof. The definition refers also to modifications described below, such as a BMP containing a specific functional sequence, e.g. heparin binding site, propeptide or the like. Such homologues or derivatives include functional derivatives of said protein, such as proteins derived from the original reindeer BMP-6 protein or any BMP from any species. The derivatives may differ in length and they may contain amino acid insertions, deletions and substitutions, as a person skilled in the art well knows. Characteristic for the bone morphogenetic protein 6 of the present invention, e.g. as disclosed in the alignment above, are the amino acids differing from the known BMP-6 proteins, such as the amino acids differing from the human counterpart, especially Pro3 and Pro16. Preferably the regions containing these amino acids are conserved in a bone morphogenetic protein of the present invention. These may be the amino acids 3-23, or more preferably amino acids 3-16, in the SEQ ID NO: 1 or homologue thereof. The amino acids 3 and 16 are prolines which have a strong effect on the folding of the mature protein and therefore also on the function of the protein. The amino acids 3 and 23 define the region containing amino acids differing from the human BMP-6 counterpart.

On the other hand, insertions, deletions and substitutions located far outside said characteristic area may not be likely to cause substantial changes in the function, effect or folding of the BMP of the present invention. For example homologues having deletions, such as deletions of few amino acids, preferably 1-10 amino acids, more preferably 1-5 amino acids, most preferably 1-3 amino acids, in carboxyl terminus or amino terminus resulting in shorter polypeptide are in the scope of the present invention as long as said deletions do not affect the characteristic amino acids of the BMP of the invention. It is preferred that said homologues have the advantageous properties of the original reindeer BMP-6 proteins, said properties being related to said characteristic amino acids and/or the region around them. Said homologues may have amino acid substitutions which do not substantially affect the function and effect of the protein of the invention. For example an amino acid not located in the active site or near it may be substituted with another amino acid having similar structural and/or chemical properties (e.g. hydrophobic or hydrophilic), i.e. conservative amino acid replacement, amino acid as long as said substitution does not substantially alter the function or folding of the mature protein. These kinds of substitutions are well known and understood in the art. Examples of such amino acid properties divided into groups are hydrophobic (Met, Ala, Val, Leu, Ile), neutral hydrophilic (Cys, Ser, Thr), acidic (Asp, Glu), basic (Asn, Gin, His, Lys, Arg), residues that influence chain orientation (Gly, Pro) and aromatic (Trp, Tyr, Phe) amino acids. Substitutions within said groups are generally not likely to cause major changes in the structure of the polypeptide backbone (e.g. a sheet or helical conformation), the charge or hydrophobicity of the molecule or the bulk of the side chain.

The homologues of the BMP of the present invention include for example any known bone morphogenetic protein which contains or has been modified to contain at least part of the conserved amino acids or sequences as described above or corresponding area in a homologous BMP in the case the numbering should differ. Also any currently unknown BMP-6 protein from any species modified as described is in the scope of the invention.

When compared to known human BMP-6 protein, the reindeer BMP-6 has seven substituted amino acids P3, G4, A10, P16, A17, S21 and A23 defined from the mature BMP-6 protein as disclosed in SEQ ID NO: 1. These amino acids are characteristic for the BMP of the present invention. More specifically P3 and/or P16 are especially characteristic for the BMP of the present invention.

In one embodiment the BMP of the present invention is any BMP or a homologue, derivative or fragment thereof containing the consensus sequence between the two prolines: P-G/S/N-R/K-R/H-Q/N-Q-A/S/N-R-N/S-R/A/K-S/A-T/S/N-P. This consensus sequence has been defined from a sequence alignment of several similar BMP-6, BMP-5 and BMP-7 proteins from different species, such as shown in the ClustalX alignment below. Said consensus sequence corresponds to the amino acids 3-16 of SEQ ID NO: 1. In still another embodiment the BMP of the present invention is any BMP or a homologue, derivative or fragment thereof containing the corresponding consensus sequence defined from BMP-6 family: P-G/S-R-R-R-Q-Q-A/S-R-N-R/A-S-T-P. Also other consensus sequences may be defined, for example ones defining an area around the second proline (Pro16 in SEQ ID NO: 1), such as R-N/S-R/A/K-S/A-T/S/N-P-A-Q-D-V, or similar sequences differing in length, e.g. by 1-5 amino acids. Such consensus sequences may be defined from the alignment below or similar alignments made by aligning different related BMP proteins. The BMP-6, BMP-5 and BMP-7 sequences aligned are from reindeer, bovine, rat, mouse, human, chicken, and African clawed frog (*Xenopus laevis*).

```
BMP6_REINDEER SAPGRRRQQARNRSTPAQDVSRASSASDYNSSELKTACRKHELYVSFQDLGWQDWIIAPK
BMP6_BOVINE   SAPGRRRQQARNASTPAQDVSRASSASDYNSSELKTACRKHELYVSFQDLGWQDWIIAPK
BMP6_RAT      SASSRRRQQSRNRSTQSQDVSRGSSASDYNSSELKTACKKHELYVSFQDLGWQDWIIAPK
BMP6_MOUSE    SASSRRRQQSRNRSTQSQDVSRGSGSSDYNGSELKTACKKHELYVSFQDLGWQDWIIAPK
BMP6_HUMAN    SASSRRRQQSRNRSTQSQDVARVSSASDYNSSELKTACRKHELYVSFQDLGWQDWIIAPK
BMP5_HUMAN    -AANKRKNQNRNKSSSHQDSSRMSSVGDYNTSEQKQACKKHELYVSFRDLGWQDWIIAPE
BMP5_CHICKEN  AANNKRKNQNRNKSSSHQESSRMPSVGDYNTSEQKQACKKHELYVSFRDLGWQDWIIAPE
BMP5_MOUSE    -AASKRKNQNRNKSNSHQDPSRMPSAGDYNTSEQKQACKKHELYVSFRDLGWQDWIIAPE
BMP7_XENOPUS  SAGGKHRNQNRSKAPKSQEALRVSNIAENSSTDQKQACKKHELYVSFKDLGWQDWIIAPE
              *  .::::* *. :   *:  *  .. .: .  :: * **:*******:*********** :

BMP6_REINDEER GYAANYCDGECSFPLNAHMNATNHAIVQTLVHLMNPEYVPKPCCAPTKLNAISVLYFDDN
BMP6_BOVINE   GYAANYCDGECSFPLNAHMNATNHAIVQTLVHLMNPEYVPKPCCAPTKLNAISVLYFDDN
BMP6_RAT      GYAANYCDGECSFPLNAHMNATNHAIVQTLVHLMNPEYVPKPCCAPTKLNAISVLYFDDN
BMP6_MOUSE    GYAANYCDGECSFPLNAHMNATNHAIVQTLVHLMNPEYVPKPCCAPTKLNAISVLYFDDN
BMP6_HUMAN    GYAANYCDGECSFPLNAHMNATNHAIVQTLVHLMNPEYVPKPCCAPTKLNAISVLYFDDN
BMP5_HUMAN    GYAAFYCDGECSFPLNAHMNATNHAIVQTLVHLMFPDHVPKPCCAPTKLNAISVLYFDDS
BMP5_CHICKEN  GYAAFYCDGECSFPLNAHMNATNHAIVQTLVHLMFPDHVPKPCCAPTKLNAISVLYFDDS
BMP5_MOUSE    GYAAFYCDGECSFPLNAHMNATNHAIVQTLVHLMFPDHVPKPCCAPTKLNAISVLYFDDS
BMP7_XENOPUS  GYAAFYCEGECAFPLNSYMNATNHAIVQTLVHFINPDTVPKPCCAPTQLNPISVLYFDDS
              **** **:***:****:.:************** :.  *: *********:**.********.

BMP6_REINDEER SNVILKKYRNMVVRACGCH (SEQ ID NO: 1)

BMP6_BOVINE   SNVILKKYRNMVVHACGCH (SEQ ID NO: 8)

BMP6_RAT      SNVILKKYRNMVVRACGCH (SEQ ID NO: 9)

BMP6_MOUSE    SNVILKKYRNMVVRACGCH (SEQ ID NO: 10)

BMP6_HUMAN    SNVILKKYRNMVVRACGCH (SEQ ID NO: 7)

BMP5_HUMAN    SNVILKKYRNMVVRSCGCH (SEQ ID NO: 11)

BMP5_CHICKEN  SNVILKKYRNMVVRSCGCH (SEQ ID NO: 12)

BMP5_MOUSE    SNVILKKYRNMVVRSCGCH (SEQ ID NO: 13)

BMP7_XENOPUS  SNVILKKYRNMVVRACGCH (SEQ ID NO: 14)
              ************** ****
```

In one embodiment of the present invention said BMP is any BMP or homologue, derivative or fragment thereof comprising the amino acids 3-16 of the SEQ ID NO: 1. Said amino acid locations are calculated from amino terminus of any general mature BMP-6 protein, such as the protein of SEQ ID NO: 1 or a homologue, derivative or fragment thereof, wherein the sequence at the amino terminus begins with SA, as for example in reindeer (see the sequence alignment above or SEQ ID NO: 1), or at a corresponding area. If there were any insertions or deletions of amino acids in the amino acid sequence of said homologue affecting the numbering, these should be taken into account when defining the location of said essential amino acids, for example by aligning the sequences as described above and then defining the locations of said amino acids. However, any of said homologues, derivatives or fragments of the BMP-6 protein should substantially have the function and efficiency disclosed herein. Because all the known BMP-6 proteins are highly conserved, defining the location of said essential prolines is unambiguous, such as in the case of human BMP-6. Also, said locations can be easily defined also from other BPMs (see the alignment above). Generally such level of homology may be at least 70%, preferably 80%, more preferably 90% and most preferably 93% at the amino acid level.

In another embodiment the BMP of the present invention is any BMP or homologue, derivative or fragment thereof containing the amino acids 3-23 of SEQ ID NO: 1. In another embodiment the BMP of the present invention is a BMP-6 protein. In still another embodiment the BMP of the present invention is a BMP or homologue, derivative or fragment thereof containing the amino acid sequence of SEQ ID NO: 1.

The homologues, derivatives or fragments mentioned in these embodiments shall contain at least one of the characteristic amino acids described above. Said homologues, derivatives or fragments do not include the known BMP-6 proteins as such, such as hBMP-6, since they do not contain said characteristic amino acids of the BMP of the present invention. However, a known BMP modified to contain at least one of said characteristic amino acids may be considered as such homologue, derivative or fragment.

One embodiment of the present invention provides the BMP as described above with a propeptide of SEQ ID NO: 2 or a functional homologue, derivative or fragment thereof. Said propeptide plays a role in the control of a BMP protein and in the proper folding of the protein. Similar propeptides are known in the art (see Regulation of bone morphogenetic protein activity by pro domains and proprotein convertases. Constam D B, Robertson E J. J Cell Biol. 1999 Jan. 11; 144(1):139-49.) The BMP propeptide or homologue thereof may be inserted in the amino terminus of a BMP protein, such as BMP-6 protein, wherein the propeptide facilitates the folding of the mature protein. Later on the propeptide may be cleaved off.

One embodiment of the present invention provides a nucleic acid molecule, such as a DNA or RNA molecule, encoding said BMP of the invention, with or without the heparin binding site or the propeptide. Because of the degeneracy of the genetic code there are a number of different nucleic acid sequences encoding the BMP of the invention, said heparin binding site or said propeptide. All such nucleic acid variants are in the scope of the present invention. Preferably said nucleic acid molecule is a DNA molecule. Non-limiting examples of said DNA sequences are disclosed in FIGS. 5-10.

One embodiment of the present invention provides a replicable nucleotide vector containing the nucleic acid molecule described above in operative association with an expression control sequence thereof. Such vector may be used for producing recombinant BMP of the present invention in a suitable host system.

The nucleic acid encoding the BMP of the invention may be inserted into said replicable vector for cloning or for expression. Various vectors are publicly available. The vector may, for example, be in the form of a plasmid, cosmid, viral particle or phage. The appropriate nucleic acid sequence may be inserted into the vector by a variety of procedures. In general, DNA is inserted into an appropriate restriction endonuclease site(s) using techniques well known in the art. Vector components may include for example one or more signal sequence(s), an origin of replication, one or more marker genes, an enhancer element, a promoter, and a transcription termination sequence. Construction of such suitable vectors containing one or more of these components employs standard ligation techniques which are well known to a person skilled in the art.

Generally said BMP may be produced recombinantly by expressing in any suitable host cell, such as bacterial host cell. Such methods are well known in the art and they are described in literature. It is essential that the protein is folded properly during the expression and it contains the necessary post-translational modifications.

It is not always possible to express and purify certain proteins properly, for example because of solubility or refolding problems. Usually E. coli can not make post-translational modifications typical for mammalian cell systems. However, the inventors of the present invention have produced recombinant reindeer BMP-6 mature part in E coli and after purification and refolding managed to prove it to be in biologically active form.

There are certain benefits when a protein, such as a BMP, is expressed in a bacterial host, such as E. coli. The protein generally shows lowered immunogenicity when compared to a similar protein expressed in for example yeast host. This may be useful later when the protein is utilized, for example administered as a medicament. E. coli produces proteins without modifications, such as glycosylation. This is particularly useful for proteins for which glycosylation is not a requirement, but which could be a problem if the protein is produced in other systems (e.g. yeast), which can over-glycosylate, or add inappropriate carbohydrates to the protein, which could lead to reduced or no activity of expressed protein and potentially create a risk of immunogenicity (Pedro de Noronha Pissarra: Recombinant DNA Proteins for the Biopharmaceutical Industry and the Future for Escherichia coli. Business Briefing: Pharma Outsourcing, London, 2004).

One embodiment of the present invention provides a host cell containing the nucleotide molecule or the nucleotide vector described above. Suitable cells include all prokaryotic and eukaryotic cells which are able to express the protein of the invention. Such host cells are well known in the art and a person skilled in the art can easily choose a suitable one. Non-limiting examples of said cells are widely used *Escherichia coli* cells, such as TOP10, Origami B (DE3) or Rosetta (DE3) strains.

Another embodiment provides a BMP produced by culturing said cell to express said protein and by recovering said expressed protein from said host cell. Any suitable methods for recovering or isolating the protein may be used and such methods are well-known in the art.

The BMP of the invention may be used for treating disorders related to bone, cartilage, tendon or periodontal defects or diseases or the like wherein regeneration, repair or growth thereof is desired, or other diseases. The protein of the invention may also be used to heal wounds, such as burns, incisions and ulcers, and to related tissue repair and also for treatment of cancer, as disclosed in EP1131087. Since BMP proteins generally lack species specificity, the patient suffering from said defect may be any suitable animal, preferably mammal, such as human, and the BMP protein used for treatment may be of any suitable origin. The use of related BMP proteins for several types of therapeutical applications is well-known in the art (see e.g. U.S. Pat. No. 6,245,889 and WO98/51354).

"Disorders related to bone, cartilage, tendon or tooth defects" as used herein refers generally to any known disorder wherein bone, cartilage, tendon or periodontal healing or reconstruction, i.e. regeneration, is desired. Non-limiting examples of treatments of disorders related to bone, cartilage, tendon or periodontal defects or diseases or the like are regeneration, repair and growth of bone and periodontal tissue; regeneration, repair and growth of bone in mammals, such as human; treatment of abnormalities of bone formation or regeneration; wound healing, ectopic bone induction and healing of segmental bone defects in vertebrates; treatment of skeletal disorders and deformations; repair of large bone defects originating from trauma, excision of tumors or congenital malformations, reconstructing bone stocks worn off by an implanted endoprothesis in revision operations and healing delayed or non-united fractures; repair of bone and cartilage defects such as critical size defects, non-critical size defects, non-union fractures, segmental non-union of fractures; acute fractures, chondral defects, osteochondral defects, subohondral defects; local bone and cartilage formation; defects resulting from degenerative diseases; dental applications such as repair of periodontal tissues, alveolar bone, cementum, tooth root membrane, filling of the tooth root canal and improvement or enhancement of fixation of the dental implant. More examples of such disorders can be found in Ann Rheum Dis, Volume 62, 2003, 73-78: Reddy A H: Cartilage morphogenetic proteins: role in joint development, homoeostasis and regeneration.

Other diseases wherein the BMP of the present invention is useful are for example cancer, fibromyalgia, psoriasis and other dermatological disorders, and rheumatic disorders and the like. Examples of such cancers and methods and compositions for treating thereof are disclosed in EP1131087.

In one embodiment the BMP of the present invention, such as BMP-6, may be provided, in any application described herein, together with one or more additional morphogenetic proteins, such as another BMP protein species or the like. Generally this provides a synergetic effect, as it is known in the art. Examples of other suitable BMP proteins are, but are not limited to, BMP-1, BMP-2, BMP-3, BMP-4, BMP-5, another BMP-6, BMP-7 and BMP-8. Also other therapeutically useful agents may be provided, such as epidermal growth factor, fibroblast growth factor and transforming growth factors (U.S. Pat. No. 6,245,889). In one embodiment said additional morphogenetic protein is originated from reindeer, such as any other reindeer BMP protein. In one embodiment the BMP of the present invention is provided as a dimer, as a homodimer or as a heterodimer together with another BMP protein as described above. In still another embodiment the BMP protein as a dimer or together with another factor or protein, as described above, is used for manufacturing medicament for treating disorders described in the specification.

In one embodiment of the present invention an osteogenic device, such as an implant, is provided containing the BMP of the invention. The osteogenic device may contain a biocompatible matrix, such as a calcium phosphate, carboxy methyl cellulose or collagen matrix or combinations thereof. In one embodiment said calcium phosphate matrix is a hydroxyapatite matrix. Said matrix may provide slow release of the BMP protein and/or the appropriate environment for presentation of the BMP protein. The osteogenic device may also contain a metal implant surrounded by said biocompatible matrix. One example of said metal is titanium. Some examples of such osteogenic devices are disclosed in WO 98/51354.

Non-limiting examples of the different framing materials, carriers or frames for forming e.g. different kinds of osteogenic devices or the like with the protein of the present invention are a medium in the form of powder, sponge, strip, film, gel, web or solution or suspension; semi-solid liquid carrier suitable for intramuscular, intravenous, intramedullary or intra-articular injection; isolated mesenchymal stem cells; any pharmaceutically acceptable vehicle; crusted auto- or allograft; any pharmaceutically acceptable matrix; a material selected from the group comprising hydroxyapatite, coral, collagen, polymers (e.g. polylactic acid, polyglycolic acid), synthetic polymers, hyaluronic acid, α-BSM, calcium phosphate, tricalcium phosphate, aporous ceramic biopolymers, aporous resorbable biopolymers, coral, demineralized bone, bioglass, any biodegradable material and combinations thereof; binding agents selected from the group comprising mannitol, dextrans, white petrolatum, alkyl and methyl celluloses, wetting agents such as sodium salt, fobrin glue, mammalian fibrinogen and thrombin and combinations and admixtures thereof. The osteogenic device may be for example a structurally stable, three-dimensional implant in form of a cube, cylinder or block or in the shape of an anatomical form or an injectable form. Examples of osteogenic devices, useful materials and techniques are disclosed in book "Skeletal reconstruction and bioimplantation" (T. Sam Lindholm, 1997, Springer-Verlag, Heidelberg, Germany).

In one embodiment of the present invention a pharmaceutical composition is provided containing a therapeutically effective amount of BMP protein of the invention together with a pharmaceutically acceptable vehicle or carrier. Said pharmaceutical compositions may be used for treating disorders related to bone, cartilage, tendon or periodontal defects or diseases, wounds and other tissue defects or any other disorders described herein.

One embodiment of the present invention provides a method for inducing the formation of bone, cartilage, tendon, tooth or the like wherein said bone, cartilage, tendon, tooth or the like is treated with the BMP of the invention or combinations thereof as described above, in vitro or in vivo. Still another embodiment of the invention provides a method for treating disorders described in the specification comprising administering the isolated BMP of the present invention to a patient suffering from said disorders. Said BMP may be administered as a pharmaceutical composition or as an osteogenic device described above. Further morphogenetic proteins or other useful agents may be administered together with said BMP of the invention, as described above, to enhance the therapeutical effect.

In the following description and examples it is described how recombinant reindeer BMPs, such as BMP-6, BMP-3c and BMP-4 mature parts with and without heparin-binding site (HBS) according to embodiments of the present invention were produced in E. coli. After purification and refolding the osteoinductive activity was verified by bioassay in mouse tight muscle pounches. The in vivo bioassay is a standard method used for assaying BMP activity since its discovery. It includes implantation of BMP in the hindquarter muscle of a mouse and estimation of heterotopic new bone induction after 10-21 days by radiology and histology.

Image analysis in determination of BMP activity is done by attenuation of X-ray beam through bone and it can be seen on the radiograph as an X-ray-positive "radioplaque" shadow compared to soft tissues. This is the basis for radiographic detection and radiomorphometric quantitation of newly formed bone after implantation of BMP or other bone inductive agent in a heterotopic or an orthotopic site.

The osteoinduction was observed in all three study groups (1 mg, 3 mg and 5 mg of recombinant reindeer BMP-6) and it was increased in dose-dependent manner (Table 2). When compared to its human counterpart the recombinant reindeer BMP-6 was proven to be more potent inducer of bone formation and could therefore be potential agent for clinical applications.

TABLE 2

Comparison of the osteoinduction responses of reindeer and human BMP-6 proteins with different doses

| | 1 mg | | | | 3 mg | | | | 5 mg | | | |
|---|---|---|---|---|---|---|---|---|---|---|---|---|
| Reindeer BMP-6 | − | (+) | − | k | − | (+) | k | (+) | + | ++ | + | − |
| Reindeer BMP-6-HBS | − | − | − | + | ++ | (+) | − | (+) | +(+) | + | +(+) | − |
| Human BMP-6 | + | − | − | (+) | − | (+) | (+) | − | + | − | (+) | − |
| Bovine BMP-6 | − | − | − | − | − | − | − | k | − | (+) | + | − |

(k = killed)

Figure 12:
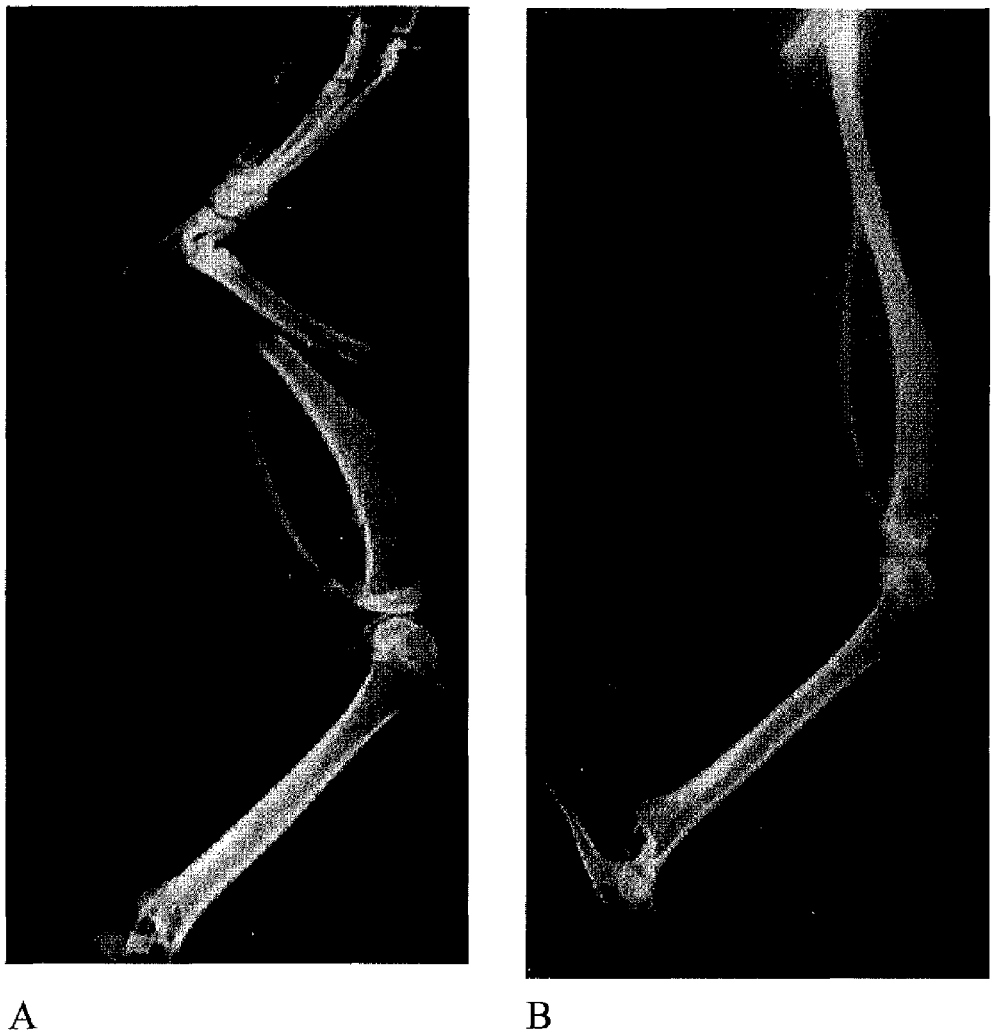
FIG. 12 shows X-ray images of a mouse hindquarter muscle, A) reference implanted with hBMP-6 and B) implanted with BMP-6 of the present invention.

The results of the in vivo bioassay are shown in FIG. 12. FIG. 12A is a reference implanted with hBMP-6 and 12B is a sample implanted with BMP-6 of the present invention. The bioassay was carried out as described in Marshall R. Urist, J. J. Chang, A. Lietze, Y. K. Huo, A. G. Brownell and R. J. DeLange (1987): Preparation and Bioassay of Bone Morphogenetic Protein and Polypeptide Fragments, Methods Enzymol 146: 294-312.

At first, there were great difficulties to get recombinant rdBMP-6 mature part expressed in E. coli. Even the mutations made to get the nucleotide sequence of rdBMP-6 to resemble the codon usage in E. coli did not seem to cause any improvement in expression level. Therefore, the inventors assumed that poor expression was caused by the high GC-content in N-terminal region of the mature part of rdBMP-6. Because heparin binding site (HBS), existing in the beginning of the reindeer BMP-2 mature part, is coded by nucleotide sequence with low GC-content, a construct in which this HBS sequence was added in front of the rdBMP-6 mature part sequence was created and this way the inventors surprisingly managed to improve the expression of recombinant rdBMP-6.

HBS located in the N-terminus of rdBMP-2 contains 10 basic amino acid residues and is reminiscent of known or postulated heparin-binding sites in other growth factors. It is possible that the interaction between protein with HBS and extracellular matrix might have an important effect on the establishment of morphogenetic gradients during development by limiting the free diffusion of a protein. Therefore, it was assumed that HBS could also improve the biological activity of recombinant rdBMP-6 by prolonging the duration of disappearance of protein from the implantation site, which was also demonstrated by bioassay.

EXAMPLES

Example 1

Cloning and Sequencing of 3'-Part of the cDNA of Reindeer BMP-6

A. RNA Isolation

The antlers of a 3-year-old male reindeer were cut off and frozen in liquid nitrogen immediately after slaughtering. The frozen antlers were cut in 0.5 cm slices and stored at −70° C. Reindeer antler mRNA was isolated using the QuickPrep® Micro mRNA Purification Kit (Pharmacia Biotech). A part of the reindeer antler slice was cut in small pieces (about 1 mm$^3$) and 0.1 g of this tissue was added to 0.6 ml of Extraction Buffer containing guanidinium thiocyanate and N-lauroyl sarcosine. The tissue was homogenized with Ultra Turrax for 3 times 10 seconds on ice and cooled between every homogenization. 1.2 ml of Elution Buffer was added and suspension was further homogenized for 1 times 10 seconds. A uniform suspension was obtained.

The reindeer antler homogenate and Oligo(dT)-Cellulose were centrifuged at top speed [14,000 rpm, RT, Centrifuge 5415 C (Eppendorf)] for 1 minute. The buffer from the Oligo(dT)-Cellulose pellet was removed and the cleared tissue homogenate was placed on the top of it. The tube was inverted to resuspend the Oligo(dT)-Cellulose pellet. The suspension was gently mixed for 5 minutes and centrifuged at top speed [14,000 rpm, RT, Centrifuge 5415 C (Eppendorf)] for 10 seconds. The supernatant was discarded.

Oligo(dT)-Cellulose was resuspended in High-Salt Buffer [10 mM Tris-HCl (pH 7.5), 1 mM EDTA, 0.5 M NaCl] and suspension was centrifuged at top speed [14,000 rpm, RT, Centrifuge 5415 C (Eppendorf)] for 10 seconds. Washings with High-Salt Buffer were repeated for 5 times and 2 additional times with Low-Salt Buffer [10 mM Tris-HCl (pH 7.5), 1 mM EDTA, 0.1 M NaCl]. 3 ml Low-Salt Buffer was added and suspension was transferred to MicroSpin Column. The MicroSpin Column was placed in Eppendorf tube and centrifuged at top speed for 5 seconds. Oligo(dT)-Cellulose in the column was rinsed for 3 times with Low-Salt Buffer.

The reindeer antler mRNA was eluted to a clean Eppendorf tube from the Micro-Spin Column by adding 0.2 ml 65° C. Elution Buffer (QuickPrep® Micro mRNA Purification Kit, Pharmacia Biotech) to the column and centrifuging at top speed [14,000 rpm, RT, Centrifuge 5415 C (Eppendorf)] for 5 seconds. The elution step was repeated twice. The isolated mRNA was precipitated by adding 5 µl of glycogen solution (5-10 mg/ml in DEPC-treated $H_2O$), 1/10 volume K Acetate solution (2.5 M potassium acetate, pH 5.0) and 0.5 ml absolute ethanol (chilled to −20° C.) to each elution. Precipitation was allowed to occur at −20° C. for at least 30 minutes and mRNA was centrifuged at top speed [14,000 rpm, 4° C., Centrifuge 5415 C (Eppendorf)] for 5 minutes. Precipitated mRNA was stored at −70° C. until cDNA synthesis was performed.

B. cDNA Synthesis

Reverse transcription of the reindeer antler mRNA was performed by modifying the instructions of the Time Saver™ cDNA Synthesis Kit (Pharmacia Biotech). 3 µg of mRNA was heat-denatured at 65° C. for 10 minutes and chilled on ice. 0.2 µmol DTT, 0.5 µg Oligo(dT)$_{12-18}$ Primer and heat-denatured mRNA were added to First strand reaction mix containing FPLCpure™ Cloned Murine Reverse Transcriptase, RNAguard™, RNase/DNase-Free BSA, dNTPs (dATP, dCTP, dGTP and dTTP) in aqueous buffer (Time Saver™ cDNA Synthesis Kit, Pharmacia Biotech). The mixed solution was incubated at 37° C. for 1 hour. After the incubation, the First strand reaction mix was added to the Second strand reaction mix containing E. coli RNase H and E. coli DNA polymerase I and dNTPs in aqueous buffer (Time Saver™ cDNA Synthesis Kit, Pharmacia Biotech). The solution was mixed gently and incubated in RT for 30 minutes. The synthesized cDNA was stored at 4° C.

C. Screening of Reindeer Antler cDNA

The part of the cDNA of the reindeer BMP-6 was amplified by PCR (Polymerase chain reaction) method using degenerative primers (5'-CGG(C)ATCTACAAGGACTGTGTT(G)G(A)TGGG-S') and (3'-GTCCGG(A)GCC(T)TGTGCCTGC-CACTAA-S') (Table 3) designed on the basis of homology of already known BMP-6 genes of the different mammalian species (human, rat and mouse). In addition to 100 ng of reindeer antler cDNA and 40 pmol of each primers the 50 µl of PCR reaction mixture contained 0.4 mM dNTPs (PCR Core Kit, Roche) and 0.7 U/µl Expand High Fidelity enzyme mix (thermostable Taq polymerase+proofreading polymerase, Roche) in Expand High Fidelity buffer with $MgCl_2$ (Expand High Fidelity PCR System, Roche). The reaction was performed under the following program using Mastercycler personal apparatus (Eppendorf): initial denaturation at 94° C. for 4 minutes and 25 cycles of denaturation 94° C. for 1 minute, annealing of the primers 55° C. for 1 minute, elongation of DNA strands 72° C. for 2 minutes. The final extension was performed at 72° C. for 10 minutes.

TABLE 3

Primers used in cloning of natural and nucleotide mutated mature part of reindeer BMP-6 Primers for cloning

```
partial cDNA of reindeer BMP-6
           5' → 3' CGG(C)ATCTACAAGGACTGTGTT(G)G
                   (A)TGGG   (SEQ ID NO: 15)

3' → 5' GTCCGG(A)GCC(T)TGTGCCTGCCACT
                   AA (SEQ ID NO: 16)

mature part of reindeer BMP-6
for pTrcHis2A 5' → 3' GGATCCGTCGGCCCCCGGGCGGCGCCGG
                      CAG (SEQ ID NO: 17)

3' → 5' AAGCTTGTGGGAGCCACAGGCCCGGACG
                      AC (SEQ ID NO: 18)

for pIVEX2.4 5' → 3' CCGCGGCTCGGCCCCCGGGCGGCGCCGG
                     CAG (SEQ ID NO: 19)
```

TABLE 3-continued

Primers used in cloning of natural and
nucleotide mutated mature part of reindeer BMP-6
Primers for cloning

|   |   |   |
|---|---|---|
|  | 3' → 5' | GCATCCTAGTGGCAGCCACAGGCCC (SEQ ID NO: 20) |
| for pTrcHBS | 5' → 3' | GGTACCTCGGCCCCGGGCGGCGCCGGC AG (SEQ ID NO: 21) |
|  | 3' → 5' | AAGCTTGTGGCAGCCACAGGCCCGGACG AC (SEQ ID NO: 22) |
| mutated mature part of reindeer BMP-6 |  |  |
| for pTrcHis2A | 5' → 3' | GGATCCGTCGGCCCCGGGGCGCCGCCGC CAG (SEQ ID NO: 23) |
|  | 3' → 5' | AAGCTTGTGGCAGCCGCAGGCGCGGACG AC (SEQ ID NO: 24) |
| for pTrcHBS | 5' → 3' | GGTACCTCGGCCCCGGGGCGCCGCCGCC AG (SEQ ID NO: 25) |
|  | 3' → 5' | AAGCTTGTGGCAGCGGCAGGCGCGGACG AC (SEQ ID NO: 26) |

D. Cloning into pGEM®-T Vector

The PCR products were purified straight from the PCR reaction mix by Wizard® PCR Preps DNA Purification System (Promega) and ligated into the pGEM®-T vector (FIG. 1.) by T4 DNA Ligase (pGEM®-T Vector System I; Promega). 0.3 µg of purified PCR product and 2.3 µg/ml of pGEM®-T vector were added to ligation buffer containing 18 mM Tris-HCl (pH 7.8), 6 mM MgCl$_2$, 6 mM DTT, 0.3 mM ATP, 3% polyethylene glycol and 0.14 U/µl T4 DNA Ligase in total volume of 66 µl. The reaction was allowed to occur at +16° C. water bath which was allowed to cool to +4° C. overnight. The newly formed plasmid was named as pMSU1 (FIG. 1).

E. The Production of Competent *Escherichia coli* TOP10 F' Cells

The competent *Escherichia coli* TOP10 F' cells were produced by the calcium chloride/magnesium chloride procedure. 2 ml of LB-medium was inoculated with *E. coli* TOP10 F' cells and grown overnight at 37° C. with shaking (225 rpm). Next morning 100 ml of fresh LB medium was inoculated with 1 ml of overnight culture and the culture was grown at 37° C. with shaking (225 rpm) to an OD$_{600}$ of 0.5-0.6. The cultured cells were collected by centrifugation (2500×g, 5 min), resuspended in 10 ml of 0.1 M MgCl$_2$ solution and collected again by centrifugation (2500×g, 5 min). After the MgCl$_2$ treatment the cells were resuspended in 10 ml of 0.1 M CaCl$_2$ solution, incubated in ice bath for 30 minutes and recollected by centrifugation (2500×g, 5 min). The CaCl$_2$ treatment was repeated except that in the second time 3.5 ml of CaCl$_2$ was used and the incubation time was 1 hour. Glycerol was added to suspension to final concentration of 14% (v/v) and the solution was divided into 200 µl portions. The competent *E. coli* TOP10 F' cells were frozen in liquid nitrogen and stored at −70° C.

F. Transformation of the Competent *Escherichia coli* TOP10 F' Cells and Selection of Clones Containing Reindeer BMP-6

The competent *Escherichia coli* TOP10 F' cells were melted in ice bath for 15 minutes. 20 µl of ligation mix (described above) was added to 100 µl of TCM (10 mM Tris-HCl, 10 mM CaCl$_2$, 10 mM MgCl$_2$, pH 7.0) and mixed with 200 µl of the competent *E. coli* cells. The mixture was incubated in ice bath for 30 minutes before the heat shock (43° C., 3 minutes). After the heat shock 800 µl of LB medium was added and the cells were allowed to regenerate for 30 minutes at 37° C. The transformed cells were collected by centrifugation at top speed for 2 minutes and resuspended to 30 µl of growth medium. The cell suspension was plated to two LB plates containing 25 µg/ml ampicillin covered with 1 mmol IPTG (isopropyl-β-D-thiogalactopyranoside) and 2.4 nmol X-gal (5-bromo-4-chloro-3-indolyl-β-D-galactoside) and the cells were grown at the plates overnight at 37° C. The positive clones were recognized by blue color formation based on α-complementation of lacZ gene. The method is described in detail in Sambrook and Russel (2001), Molecular Cloning, Cold Spring Harbor Laboratory Press, New York.

G. Isolation of pMSU1 Plasmids and Sequencing of cDNA Inserts

The plasmids were isolated by Wizard® Plus Minipreps DNA Purification System (Promega) and then further purified by ethanol precipitation. The cDNA identity was confirmed by sequencing with ABI Prism (Perkin-Elmer Corporation). The sequencing reaction was performed using DYEnamic ET Terminator Cycle Sequencing Kit (Amersham Pharmacia Biotech) and Mastercycler Personel apparatus (Eppendorf). The primers in the PCR reaction for sequencing were (5'-TAATACGACTCACTATAGGGCGA-3') (SEQ ID NO: 27) and (3'-ATTTAGGTAACACTATAGAATAC-5') (SEQ ID NO: 28) (Table 4) and the program was as follows: 25 cycles of denaturation 94° C. for 30 seconds, annealing 50° C. for 15 seconds, elongation for 60° C. The amplified PCR products were precipitated by ethanol precipitation method. In 10 µl reaction 1 µl of 1.5 M Na-acetate-250 mM EDTA buffer and 95-100% ethanol was added so that the final ethanol concentration was 75%. The precipitation was allowed to occur in ice bath for 7 minutes and then the mixture was centrifuged for 20 minutes. The supernatant was discarded and the pellet was washed with 125 µl of 70% ethanol in RT. The solution was centrifuged briefly and the washing ethanol was removed as precisely as possible. The pellet was dried in 37° C. for a few minutes until all the ethanol was completely fumed. The ABI Prism apparatus was located in Department of medical biochemistry and molecular biology, University of Oulu, Finland and the final sequencing was performed there. The nucleotide sequence and the corresponding amino acid sequence of partial cDNA of reindeer BMP-6 is seen in FIG. 10.

TABLE 4

Primers used in sequencing of natural and
nucleotide mutated mature part of reindeer BMP-6
Primers for sequencing

|   |   |   |
|---|---|---|
| pGEM-T ® plasmids | 5' → 3' | TAATACGACTCACTATAGGGCGA (SEQ ID NO:27) |
|  | 3' → 5' | ATTTAGGTGACACTATAGAATAC (SEQ ID NO: 28) |
| pTrcHis2A plasmids | 5' → 3' | AGAGGTATATATTAATGTATCG (SEQ ID NO: 29) |
|  | 3' → 5' | ATGGTCGACGGCGCTATTCAG (SEQ ID NO: 30) |
| pIVEX2.4c plasmids | 5' → 3' | TAATACGACTCACTATAGGGCGA (SEQ ID NO: 31) |
|  | 3' → 5' | GCTAGTTATTGCTCAGCGG (SEQ ID NO: 32) |

Example 2

Expression of the Natural and Nucleotide Mutated Recombinant Reindeer BMP-6 Mature Part in *Escherichia coli* TOP10 F', Origami B (DE3) and Rosetta (DE3) Cells A. Amplification of the Mature Part of Reindeer BMP-6 for Expression Vector The mature part of reindeer BMP-6 was amplified from the pMS1H plasmid by PCR method using homology primers (5'-GGATCCGTCGGCCCCCGGGCGGCGCCGGCAG-3') (SEQ ID NO: 17) and (3'-AAGCTTGTGGCAGCCACAG-GCCCGGACGAC-5') (SEQ ID NO: 18) and for nucleotide mutated mature part version (5'-GGATCCGTCGGC-CCCCGGGGCGCCGCCGCCAG-3') (SEQ ID NO: 17) and (5'-AAGCTTGTGGCAGCCGCAGGCGCGGACGAC-3') (SEQ ID NO: 24) (see Example 2 Part B). Primers are also seen in Table 3. There were recognition sites for restriction enzymes Bam HI and Hind III at the 5'- and 3'-end of primers respectively.

In addition to 0.05 μg of pMSU plasmid and 40 pmol of each primers the 50 μl of PCR reaction mixtures contained 0.4 mM dNTPs (PCR Core Kit, Roche) and 0.7 U/μl Expand High Fidelity enzyme mix (thermostable Taq polymerase+ proofreading polymerase, Roche) in Expand High Fidelity buffer with $MgCl_2$ (Roche). The PCR reactions were performed under the following program using Mastercycler personal apparatus (Eppendorf): initial denaturation at 94° C. for 4 minutes and 25 cycles of denaturation 94° C. for 1 minute, annealing of the primers 55° C. for 1 minute, elongation of DNA strands 72° C. for 2 minutes. The final extension was performed at 72° C. for 10 minutes. The PCR products were purified directly from the PCR reaction mixtures using Wizard® PCR Preps (Promega) and ligated to the pGEM®-T vectors. The newly formed plasmids with the natural and nucleotide mutated mature part of the reindeer BMP-6 were named as pMU2 and pMU8, respectively (FIG. 1).

B. Subcloning of the Natural and Nucleotide Mutated Mature Part of Reindeer BMP-6 from pGEM®-T vector to the Expression Vector pTrcHis 2A (Invitrogen) and Transformation of the Competent *Escherichia coli* TOP10 F', Origami B (DE3) and Rosetta (DE3) Cells The subcloning of the natural and nucleotide mutated mature part of reindeer BMP-6 from pGEM®-T vector to the expression vector pTrcHis 2A (FIG. 2) was accomplished by first digesting the mature parts off from pGEM®-T vector using Bam HI and Hind III restriction enzymes and then ligating the inserts to pTrcHis 2A digested with the same enzymes. The Bam HI (Roche) and Hind III (Roche) digestion of pGEM®-T constructs and pTrcHis 2A (1 μg) was performed in 10 μl of 10 mM Tris-HCl, 10 mM NaCl, 5 mM $MgCl_2$, 1 mM 2-mercaptoethanol, pH 8.0 (SuRE/Cut Buffer B, Roche) with 1 U/μl of each restriction enzyme. The reactions were allowed to occur for 1.5 hours in 37° C. and then the restriction enzymes were inactivated by heating in 65° C. for 20 minutes and freezing in −20° C. Ligation was performed in 2× Rapid Ligation Buffer (supplied with pGEM®-T vector by Promega) in +16° C. water bath which was allowed slowly to cool down to +4° C. overnight (ligase concentration 0.1 U/μl).

Figure 2:
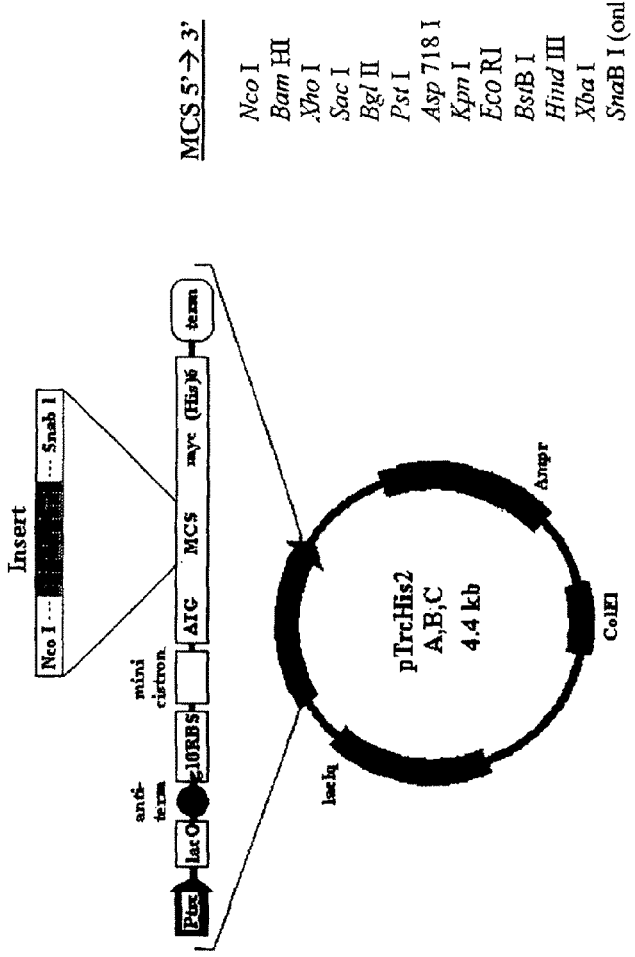
FIG. 2 shows plasmids containing various inserts in expression vector pTrcHis2A (Invitrogen).

The newly formed constructs were checked by sequencing (protocol is described in Example 1 Part G) using primers (5"-AGAGGTATATATTAATGTATCG-3') (SEQ ID NO: 29) and (3'-ATGGTCGACGGCGCTATTCAG-5') (SEQ ID NO: 30) (Table 4). Expression vector containing pTrcHis 2A plus the natural reindeer BMP-6 mature part cDNA and pTrcHis 2A plus the nucleotide mutated reindeer BMP-6 mature part cDNA were named as pMU20 and pMU90, respectively (FIG. 2). The competent *Escherichia coli* TOP10 F' cells were transformed as described in Example 1 Part F and Origami B (DE3) and Rosetta (DE3) cells were transformed following the instructions of the user manual shipped with the competent cells (Novagen).

C. Nucleotide Mutations to Make the Codons of the Natural Mature Part of Reindeer BMP-6 More Suitable for *Escherichia coli* Codon Usage To get the highest expression possible, eight codons in the mature part of reindeer BMP-6 were mutated to more common ones in *E. coli*. The mutated codons coded amino acids P6, R8, R10, P99, P103, R132, R137 and C139 (FIG. 5). Due to mutations the codon frequencies of used codons were raised dramatically (differences are described in Table 6). Mutations P6, R8, R10, R137 and C139 were performed using PCR technique (see Example 2 Part A) and mutations P99, P103 and R132 were performed after the mature part subcloning into pTrcHis 2A (see Example 2 Part B) by Quick-Change™ Site-Directed Mutagenesis Kit (Stratagene) following the instructions of the kit manual. The oligos used in the mutations performed by the kit are shown in Table 5.

TABLE 5

Primers used in for mutations of reindeer BMP-6
Primers for additional mutations (pMU80 → pMU90)

| | | |
|---|---|---|
| P99 and P103 | 5' → 3' | CCTCATGAACCCGGAGTACGTCCCGAAGCCGTGC TGTGCG (SEQ ID NO: 33) |
| | 3' → 5' | CGCACAGCACGGCTTCGGGACGTACTCCGGGTTC ATGAGG (SEQ ID NO: 34) |
| R132 | 5' → 3' | CCTGAAAAAGTACCGCAACATGGTCGTCCGCGCC (SEQ ID NO: 35) |
| | 3' → 5' | GGCGCGGACGACCATGTTGCGGTACTTTTTCAGG (SEQ ID NO: 36) |

TABLE 6

Changes in amino acid codon frequencies in reindeer BMP-6 mature part caused by site directed nucleotide mutations. Amino acids are numbered according to sequence of recombinant rdBMP-6 produced from plasmid pMU90 (see FIG. 5).

| Amino acid | Natural codon/ frequence | Mutated codon/ frequence |
|---|---|---|
| P6 | ccc/5.1 | ccg/22.0 |
| R8 | cgg/5.4 | cgc/20.6 |
| R10 | cgg/5.4 | cgc/20.6 |
| P99 | ccc/5.1 | ccg/22.0 |
| P103 | ccc/5.1 | ccg/22.0 |
| R132 | agg/1.7 | cgc/20.6 |
| R137 | cgg/5.4 | cgc/20.6 |
| C139 | tgt/5.1 | tgc/6.2 |

Figure 3:
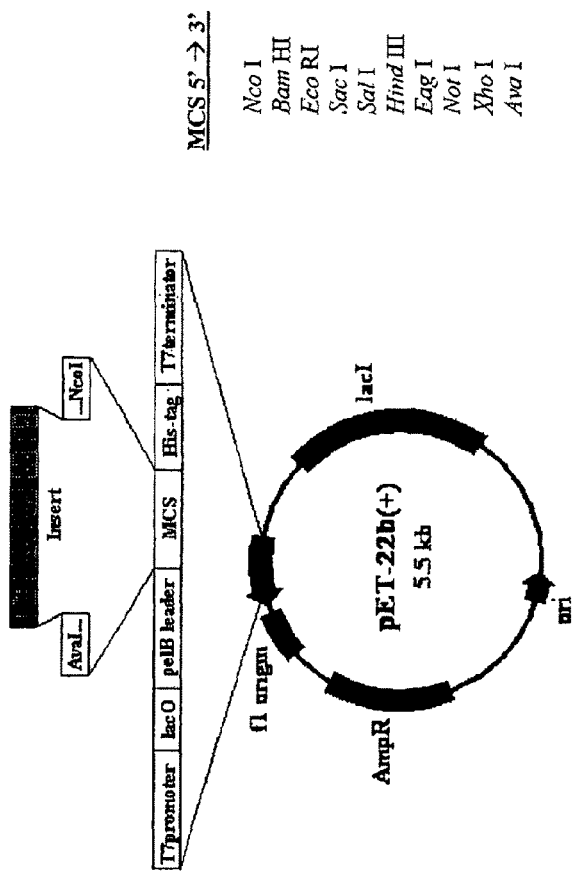
FIG. 3 shows plasmids containing various inserts in expression vector pET-22b(+) (Novagen).

D. Insertion of the Natural and Nucleotide Mutated Mature Part of Reindeer BMP-6 to the Expression Vector pET22b(+) (Novagen) and Transformation of the Competent *Escherichia coli* Origami B (DE3) and Rosetta (DE3) Cells The subcloning of the natural and nucleotide mutated mature part of reindeer BMP-6 to the expression vector pET22b(+) (Novagen) (FIG. 3) was performed as described above (see Example 2 Part B). The newly formed plasmids containing pET22b(+) plus the natural reindeer BMP-6 mature part cDNA and pET22b(+) plus the nucleotide mutated reindeer BMP-6 mature part cDNA were named as pETrd6A and pETrd6, respectively (FIG. 3). Transformations of Origami B (DE3) and Rosetta (DE3) cells were performed as described above.

E. Expression of the Recombinant Reindeer BMP-6 Mature Part in *Escherichia coli* Cell Cultures and Collection of the Cells

*E. coli* cells [TOP10, Origami B (DE3) and Rosetta (DE3)] containing either pMU20, pMU90, pETrd6A or pETrd6 were grown overnight in 50 ml of SOB medium containing ampicillin (50 μg/ml) and for Rosetta (DE3) cells also chloramphenicol (35 μg/ml) in +37° C. with shaking (225 rpm). Next morning 1200 ml of SOB medium, containing antibiotics mentioned above, was inoculated with 24 ml of overnight culture and incubated in +37° C. with shaking (225 rpm) until $OD_{600}$ was 0.6 when the cells were in mid-log phase. At this point the recombinant protein expression was induced by adding IPTG to final concentration 1 mM. After the induction the cells were grown additional 4 to 5 hours and then collected by centrifugation. The amino acid sequences of the recombinant proteins produced with respective nucleotide sequences are presented in FIG. 5 (pMU20/pMU90) and FIG. 7 (pETrd6A/pETrd6).

Example 3

Purification and Refolding of Nucleotide Mutated Recombinant Reindeer BMP-6 Mature Part A. Washing of Inclusion Bodies Collected cells were suspended in 50 mM Na-phosphate buffer (pH 7.0, 220 g cells/1 liter of buffer) by shaking. Suspension was centrifuged in 5,500 g for 45 minutes in +40° C. Washing with Na-phosphate was repeated once. Cell pellet was weighted and stored in −70° C. overnight. Frozen pellet with partly erupted cells was thawed and suspended in 20 mM Tris-HCl buffer with 0.5 mM EDTA (pH 8.5, 25 mg/ml) by shaking 2 minutes. Suspension was centrifuged 26,000 g for 30 minutes in +4° C. and Tris-HCl-EDTA washing was repeated once. The remaining pellet was weighted. In last washing step, pellet was suspended (200 rpm/minute, overnight, RT) in lysis buffer 6 M GuHCl-20 mM Na-phosphate-0.5 M NaCl (pH 8.0, 35 mg/ml) when all the remaining intact *E. coli* cells are erupted and inclusion bodies made soluble. Suspension was centrifuged (26,000 g, 45 min, RT), pellet discarded and recombinant protein in soluble form in remaining supernatant. Finally, to be sure to get rid of all cell remnants, supernatant was filtered through 45 μm filter.

B. Precipitation According to Isoelectric Point (pI)

The nucleotide mutated recombinant reindeer BMP-6 expressed from pETrd6 in *Escherichia coli* Origami B (DE3) or Rosetta (DE3) cells was precipitated by isoelectric precipitation in pH 9.69. Isoelectric point was determined by computer calculations according to amino acid sequence of the recombinant reindeer BMP-6 (FIG. 7). The precipitant was collected by centrifugation (12,000×g, 30 min, RT) and resuspended in lysis buffer (6 M GuHCl-20 mM Na-phosphate-0.5 M NaCl; pH 8.0).

C. Immobilized Metal Affinity Chromatography (IMAC)

*Escherichia coli* cells were lysed by shaking in 6 M GuHCl-20 mM Na-phosphate-0.5 M NaCl (pH 8.0) for 2 hours and filtrated through 45 μm filter. In IMAC method, pre-packed HiTrap Chelating HP affinity columns (Amersham Pharmacia Biotech) were used. Columns were charged with $Co^{2+}$, $Cu^{2+}$ or $Ni^{2+}$ ions according to instruction manual applied by supplier. The aid of the use of the his-tag-epitope at the end of the rdBMP-6 protein was that the his-tag-epitope bound up in the metal ion charged column and the impurities caused from *E. coli* cell debris flow through. After column charging, filtered supernatant from washing steps was applied in column. Majority of impurities was removed by washing the column with lysis buffer (6 M GuHCl-20 mM Na-phosphate-0.5 M NaCl, pH 8.0) 5-10 times bed volume. Second washing was performed with 5-10 times bed volume of buffer in which 6 M GuHCl of lysis buffer was replaced by 6 M Urea. Recombinant reindeer BMP-6 was eluted from the HiTrap column by pH gradient from pH 7.0 to pH 4.0 (6 M Urea-20 mM Na-phosphate-0.5 M NaCl). The fractions were analyzed by SDS-PAGE and the ones containing approximately pure rdBMP-6 were combined for refolding of recombinant protein.

D. Refolding of Recombinant rdBMP-6 Mature Part

The BMP-6 fractions analyzed by SDS-PAGE were pooled and dialyzed against water. After dialysis precipitated protein was collected by centrifugation and resuspended in 8 M Urea, 0.1 M Tris/HCl, pH 8 in the presence of 100 mM DTT, 1 mM EDTA and incubated for 2 h at 25 degrees. The pH was lowered to pH 3-4 by drop wise addition of 1 M HCl. The DTT was removed completely by dialysis against 6 M urea, 10 mM HCl for 2 h at 25° C. Dialysis was continued at 4° C. overnight against 6 M urea. Refolding of recombinant rdBMP-6 was performed by two-step dialysis. The first dialysis solution was 20 mM Tris-HCl-150 mM NaCl-3 M urea (pH 7.5). The dialysis buffer was changed at least six times during two to three days. Desalted sample was centrifuged and pellet was dried by lyophilization. At that point the purity of BMP-6 was 75% and its refolding measured by non-reducing SDS-PAGE was 50%. Quantification of the refold dimer of recombinant reindeer BMP-6 on Coomassie Brilliant Blue stained gels was done densitometrically.

Example 4

Addition of Heparin Binding Site in Front of the Mature Part of the Reindeer BMP-6

A. Addition of Heparin Binding Site Coding DNA Fragment to pTrcHis 2A Vector

Two complementary primers seen in Table 7 were designed using heparin binding site (HBS) of the reindeer BMP-2 as a model. Bam HI and Kpn I restriction sites were added in 5' and 3' ends of HBS, respectively. The primers were first denatured in +100° C. for 5 min and then annealed by allowing a small +100° C. water bath to cool down to room temperature and further to +4° C. (1 h). Both annealed HBS fragment (1 μg) and pTrcHis 2A vector (0.5 μg) were digested by Bam HI (1 U/μl) and Kpn I (2 U/μl) in Multi-Core buffer (Promega) in +37° C. for 1.5 hours and ligated in +16° C. water bath which was allowed to cool down to +4° C. overnight. The newly formed construct was checked by sequencing (see Example 2 Part B) and named pTrcHBS (FIG. 2).

TABLE 7

Primers used in cloning of nucleotide mutated
mature part of reindeer BMP-6
Primers for HBS cloning

5' → 3' CGGGATCCGCAAGCAAAACATAAACAGCGCAAACGCGGTACC
        CC (SEQ ID NO: 37)

3' → 5' GGGGTACCGCGTTTGCGCTGTTTATGTTTTGCTTGCGGATCC
        CG (SEQ ID NO: 38)

B. Addition of the Natural and Nucleotide Mutated Mature Part of Reindeer BMP-6 to pTrcHBS and Transformation the Competent *Escherichia coli* TOP10 F', Origami B (DE3) and Rosetta (DE3) Cells For the addition of the natural and nucleotide mutated mature part of reindeer BMP-6 to pTrcHBS, the mature part was amplified from pMSU1 (FIG. 1). In the primers used there was Kpn I restriction site in the beginning of the 5' end primers and Hind III restriction site at the end of the 3' primers. The primers for amplification of the natural mature part reindeer BMP-6 were (5'-GGTACCTCGGC-CCCCGGGCGGCGCCGGCAG-3') (SEQ ID NO: 21) and (5'-AAGCTTGTGGCAGCCACAGGCCCGGACGAC-3') (SEQ ID NO: 22) and for the amplification of the nucleotide mutated mature part of reindeer BMP-6 (5'-GGTAC-CTCGGCCCCGGGGCGCCGCCGCCAG-3') (SEQ ID NO: 25) and (5'-AAGCTTGTGGCAGCCACAGGCCCGGAC-GAC-3') (SEQ ID NO: 26). The primers are also shown in Table 3. PCR reactions, purification of PCR products and ligation reactions to pGEM®-T vector were performed as described in Example 1 Part C and D. pGEM®-T vector containing the natural mature part of reindeer BMP-6 was named pMU12 and pGEM®-T vector containing nucleotide mutated mature part of reindeer BMP-6 was called pMU11. Both constructs are schematically presented in FIG. 1.

The subcloning of the nucleotide mutated mature part of reindeer BMP-6 from pGEM®-T vector to pTrcHBS was accomplished by the same way as the subcloning of same inserts into pTrcHis 2A described in Example 2 Part B. The only exception was that Bam HI was replaced by Kpn I and the buffer used was Multi-Core buffer supplied by Promega. Transformations were performed as described in Example 1 Part F and in Example 2 Part B. The new constructs were named pTrcHBSrd6A (natural mature part) and pTrcHBSrd6 (nucleotide mutated mature part) (FIG. 2) and both constructs were checked by sequencing (see Example 2 Part C).

C. Insertion of the Natural and Nucleotide Mutated Mature Part of Reindeer BMP-6 with Heparin Binding Site to pET22b(+) and Transformation the Competent *Escherichia coli* Origami B (DE3) and Rosetta (DE3) Cells Insertion of the natural and nucleotide mutated mature part of reindeer BMP-6 with heparin binding site to pET22b(+) was performed exactly the same way as the subcloning of the natural and nucleotide mutated mature part of reindeer BMP-6 from pGEM®-T vector to the expression vector pTrcHis 2A described in Example 2 Part B. Transformations were performed as described in Example 1 Part F and in Example 2 Part C. The new constructs were named pETHBSrd6A (the natural mature part of reindeer BMP-6) and pETHBSrd6 (the nucleotide mutated mature part of reindeer BMP-6) (FIG. 3).

D. Expression of the Recombinant Reindeer BMP-6 Mature Part with Heparin binding Site in *Escherichia coli* Cell Cultures and Collection of the Cells The expression was performed as described earlier in Example 2 Part E. The amino acid sequences of the recombinant proteins with respective nucleotide sequences were presented in FIG. 6 (pTrcHBSrd6A/pTrcHBSrd6) and FIG. 8 (pETHBSrd6A/pETHBSrd6).

Example 5

Purification and Refolding of Nucleotide Mutated Recombinant Reindeer BMP-6 Mature Part With Heparin Binding Site (HBSrdBMP-6)

A. IMAC Purification for HBSrdBMP-6

*Escherichia coli* cells were lysed by shaking in 6 M GuHCl-20 mM Na-phosphate-0.5 M NaCl (pH 8.0) for 2 hours and filtrated through 45 µm filter. In IMAC purification method, pre-packed HiTrap Chelating HP affinity columns (Amersham Pharmacia Biotech) were used. Columns were charged with $Co^{2+}$, $Cu^{2+}$ or $Ni^{2+}$ ions according to instruction manual applied by supplier. Filtrated lysate was applied to the column and washed with 15 times the bed volume of lysis buffer. Second washing step was performed by 40 times the bed volume of 6 M Urea-20 mM Na-phosphate-0.5 M NaCl (pH 7.5). In third washing buffer there was 0.05 M imidazole added into second washing buffer and the washing volume was 15 times the bed volume. Recombinant HBSrdBMP-6 was eluted from the column by imidazole gradient from 0.05 M to 500 mM in 6 M Urea-20 mM Na-phosphate-0.5 M NaCl (pH 7.5). The fractions were analyzed by SDS-PAGE and the ones containing the most highly purified recombinant HBSrdBMP-6 were combined and dialyzed against 100 mM Na-phosphate buffer (pH 7.5) over the weekend. Precipitated recombinant protein was colleted by centrifugation and solved in 8 M Urea-100 mM Na-phosphate-10 mM Tris-HCl (pH 7.5). Before Heparin affinity column purification the recombinant protein solution was filtrated through 45 µm filter.

B. Heparin Affinity Column Purification for Recombinant HBSrdBMP-6

Filtrate obtained after IMAC purification was applied in ready-to-use HiTrap Heparin HP column (Amersham Pharmacia Biotech) which was balanced with 8 M Urea100 mM Na-phosphate-10 mM Tris-HCl (pH 7.5). The column was then washed with 20 times bed volume of the same buffer and recombinant HBSrdBMP-6 was eluted from the heparin column by NaCl gradient from 0 M to 2 M also in the same buffer. The fractions analyzed by SDS-PAGE and Western blot analysis with the highest purity of HBSrdBMP-6 were combined. In Western blot analysis specific antibodies against His6 and BMP-6 were used. Combined fractions were ready for refolding procedure.

C. Refolding of Recombinant HBSrdBMP-6

Refolding of recombinant HBSrdBMP-6 was performed as described in Example 3 part D for recombinant rdBMP-6.

Example 6

The Biological Activity Test of Nucleotide Mutated Recombinant Reindeer BMP-6 Mature Part With and Without Heparin Binding Site The biological activity of the lyophilized recombinant HBSrdBMP-6 was tested by implanting less than one mg of recombinant HBSrdBMP-6 absorbed into Lyostrypt® collagen sponge in mouse tight muscle pouches. After 21 days the hind legs were roentgenographed and the implant sites dissected and fixed in 10% neutral formalin solution. Fixed implants were cut into 4 µm sections and stained with hematoxylin-eosin. Sections were examined with a light microscope.

A new bone formation as an area and optical density was evaluated by radiographs. The radiographic images were transferred into a computer by using an optical scanner (HP Scan Jet, Hewlett Packard, USA). Ectopic and orthopic new bone formations were evaluated as the areas ($mm^2$) of calcified tissue visible in the radiographs defined by using the Scion Image Beta 4.02 (Scion Corp., USA) software. The mean optical density (mmAl) of the defined area was measured with the same equipment. Calibration of the optical density was performed by using an aluminum wedge (Al) with 0.25 mmAl steps, giving a calibrated density range up to 4 mmAl.

As a comparison, the biological activity of recombinant human BMP-6 mature part produced by the same method was also tested using bioassay described above.

Example 7

Expression of the Recombinant Reindeer BMP-6 Mature Part in Rapid Translation System RTS 500

A. Construction of the RTS 500 Expression Vector pIVEX2.4c (Roche)

Figure 4:
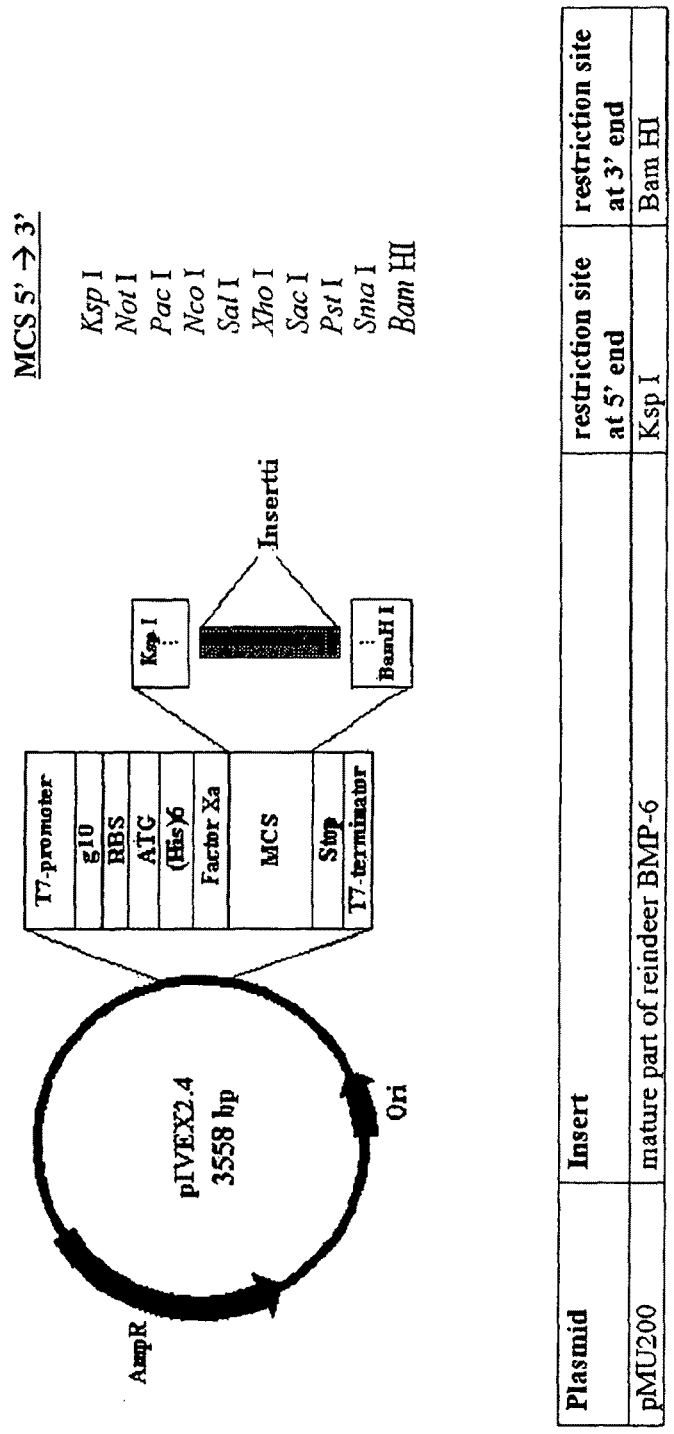
FIG. 4 shows a plasmid containing insert in RTS500 expression vector pIVEX2.4c (Roche).

The amplification of the natural mature part of reindeer BMP-6, purification of the PCR product, the ligation into pGEM®-T vector (FIG. 1), the competent *Escherichia coli* TOP10 F cell transformation, plasmid purification and the sequencing of the inserts were performed the same way as described in Example except that the primers for amplification of the mature part of reindeer BMP-6 were (5'-CCGCG-GCTCGGCCCCCGGGCGGCGC-3') (SEQ ID NO: 19) and (3'-GGATCCTAGTG GCAGCCACAGGCCC-5') (SEQ ID NO: 20) (Table 3) and the construct was named pMU2/2 (FIG. 1). Primers for sequencing the construct were (5'-TAATACGACTCACTATAGGGCGA-3') (SEQ ID NO: 31) and (3'-GCTAGTTATTGCTCAGCGG-5') (SEQ ID NO: 32) (table 4). In the amplification primers there were recognition sites for restriction enzymes Ksp I (Sac II) and Bam H1 at the 5'- and 3'-end of primers, respectively and they were utilized in subcloning of the natural mature part of reindeer BMP-6. Plasmids pMU2/2 and p1VEX 2.4c (0.5 µg) were digested in 10 µl volume of 10 mM Tris-HCl, 10 mM MgCl$_2$, 1 mM dithioerythritol, pH 7.5 (SuRE Cut Buffer L, Roche) with 1 U/µl of each restriction enzyme. The restriction enzymes were inactivated before the ligation and the ligation reaction was performed as described in Example 2 Part C. The newly formed construct was named as pMU500 (FIG. 4).

B. Production of the Recombinant BMP-6 Mature Part in RTS 500

The RTS 500 reaction was performed following the instructions of Rapid Translation System RTS 500 *E. coli* Circular Template Kit Instruction Manual. The amino acid sequence of the recombinant protein with respective nucleotide sequence is presented in FIG. 9.

Example 8

Addition of Heparin Binding Site in Front of the Mature Part of the Reindeer BMP-3c/138, BMP-3c/110 and BMP-4/116

Construction of BMP-3c and BMP-4 Vectors with Heparin Binding Site (HBS)

KpnI restriction sites were created in front of the mature parts of rdBMP-3c/138, BMP-3c/110 and rdBMP-4 with PCR method (Example 2A). Templates in these reactions were BMP genes cloned previously in pTrcHis2A vector between BamHI and HindIII restriction sites. Primers (Sigma-Genosys) designed for these reactions are in table 8.

TABLE 8

Primers used in PCR reaction creating KpnI and HindIII restriction sites in BMPs

| gene | primer |
|---|---|
| BMP-3c/138 | 5' 5' GGTACCAGGAAGAAGGGCCAGGATGTTTTC 3' (SEQ ID NO: 40) |

TABLE 8-continued

Primers used in PCR reaction creating KpnI and HindIII restriction sites in BMPs

| gene | primer |
|---|---|
| | 3' 5' AAGCTTTTGGCAGGCACAGGTCTCCACAG 3' (SEQ ID NO: 41) |
| BMP-3c/110 | 5' 5' GGTACCCAATGGGATGAGCCACGGGTC 3' (SEQ ID NO: 42) |
| | 3' 5' AAGCTTTTGGCAGGCACAGGTCTCCACAG 3' (SEQ ID NO: 43) |
| BMP-4/116 | 5' 5' CAGGTACCAGCCCCAAGCATCACCCACAG 3' (SEQ ID NO: 44) |
| | 3' 5' AAGCTTGCGGCACCCACATCCCTCCAC 3' (SEQ ID NO: 45) |

For the construction of HBS variants of rdBMPs above, the mature parts of reindeer BMP-3c/138, BMP-3c/110 and BMP-4 were amplified from cDNAs cloned in pTrcHis2A. After that all the mature parts were ligated into pTrcHBS (see the construction of pTrcHBS in Example 4, part A) and three different heparin binding site containing vectors were formed. They were named pTrcHBSrd3c/138, pTrcHBSrd3c/110 and pTrcHBSrd4.

B. Expression, Purification and Refolding of pTrcHBSrd3c/138, pTrcHBSrd3c/110 and pTrcHBSrd4, in *E. coli* TOP10 Produced Proteins.

Expression tests were done as described earlier (Example 2, part E). All of the three different BMP proteins were produced in TOP10 *E. coli* cells and the produced cells were harvested and collected by centrifugation. After that, the collected cells were first washed several times and erupted, lysed and finally filtered the soluble recombinant BMP proteins in inclusion body form to get the proteins free from cell remnants (see Example 3, part A).

Immobilized metal affinity chromatography (IMAC) was used to purify the BMP proteins. Pre-packed HiTrap Chelating HP affinity columns (Amersham Biosciences) were charged with $Co^{2+}$, $Cu^{2+}$ or $Ni^{2+}$ ions according to manufactures procedure. Filtered supernatant of reindeer recombinant proteins was applied in column. After washing the column several times (Example 3, part C) the most of the impurities was removed. The purified proteins were eluted from the column by pH gradient (Example 3, part C), analyzed by SDS-PAGE and used for the refolding experiments.

For the refolding the fractions from HiTrap column were pooled and dialyzed against water. After dialysis precipitated protein was collected and resuspended in denaturing buffer (Example 3, part D). The pH was lowered to pH 3-4 and DTT was removed by dialysis. The refolding of recombinant reindeer BMPs with HBS was performed by two-step dialysis as described in Example 3, part D. The amounts of refolded proteins were defined by non-reducing SDS-PAGE.

C. The Biological Activity Test of Recombinant Reindeer BMP-3c and BMP-4 With Heparin Binding Site The biological activity was tested by implanting recombinant BMP proteins absorbed into collagen sponge in mouse tight muscle pouches (see Example 6). Ectopic and orthopic new bone formation were evaluated as the areas ($mm^2$) of calcified tissue visible in the radiographs defined by using the Scion Image Beta 4.02 (Scion Corp., USA) software (Example 6).

Results
Cloning of Partial cDNA of Reindeer BMP-6

The nucleotide sequence obtained from ABI Prism reactions was analyzed with computer and it was compared to already known BMP sequences. Due to homology searches the newly cloned cDNA seemed to be most homological with bovine BMP-6 (nucleotide homology 95.0% and amino acid homology 99.1%). Nucleotide and amino acid homologies of BMP-6 proteins between mammalian species are presented in Table 1. The nucleotide sequence of reindeer BMP-6 and the corresponding amino acid sequence of partial cDNA of reindeer BMP-6 are shown in FIG. 10.

Expression of Reindeer BMP-6 Mature Part

First, the mature part of reindeer BMP-6 was cloned in pTrcHis2A vector and *E. coli* TOP 10 cells were transformed by resulted pMU20 vector. Expression of recombinant protein was induced by IPTG. Recombinant protein production was checked in SDS-PAGE, but no induction was observed. This was expected to be caused by several codons in rdBMP-6 which were rare for *E. coli* codon usage. These codons were mutated to be more suitable for *E. coli* protein translation and plasmid pMU90 was created. Yet, when analyzed in SDS-PAGE no recombinant protein induction was still observed. It was concluded that this could possibly be caused by high GC content in the beginning of the rdBMP-6. It was also noticed that heparin binding site existing in the beginning of reindeer BMP-2 mature part had very low GC content and by adding it in front of reindeer BMP-6 mature part it could also be utilized as a part of the purification procedure. Therefore, pTrcHBS vector was constructed. By cloning the natural rdBMP-6 mature part and nucleotide mutated rdBMP-6 mature part in pTrcHBS the vectors pTrcHBSrd6A and pTrcHBSrd6 were obtained. Successful induction of both recombinant HBSrdBMP-6A and HBSrdBMP-6 was verified by SDS-PAGE but the expression level of nucleotide mutated HBSrdBMP-6 was significantly higher.

Because there still was not the vector for producing the plain recombinant rdBMP-6 mature part it was decided to try another vector system with different *E. coli* cell lines. pET22b (+) (Novagen) with His6-tag and pelB leader was chosen as the new expression vector and Rosetta (DE3) and Origami B (DE3) *E. coli* lines were chosen for expression. The natural and nucleotide mutated reindeer BMP-6 mature part was cloned with and without heparin binding site to pET22b(+) and four new plasmids were named as pETrd6A, pETrd6, pETHBSrd6A and pETHBSrd6 and both Rosetta (DE3) and Origami B (DE3) cells were transformed with all of them separately. When analyzed by SDS-PAGE, expression of rdBMP-6 or HBSrdBMP-6 was observed with every combination. Nevertheless, as described earlier with pTrcHBSrd6A and pTrcHBSrd6, the nucleotide mutations in mature region caused dramatic increase in expression level when expressing either plain mature part of reindeer BMP-6 or mature part of reindeer BMP-6 with heparin binding site. Due to expression studies mainly Rosetta (DE3) cells with pETrd6 and pETHBSrd6 vectors were used in producing recombinant rdBMP-6 and HBSrdBMP-6, respectively.

Purification of rdBMP-6

Recombinant reindeer rdBMP-6 protein was overexpressed in *E. coli*. After the wash treatment, isoelectric point precipitation and solubilization of the inclusion bodies the content of recombinant reindeer rdBMP-6 was 85%.

Figure 11:
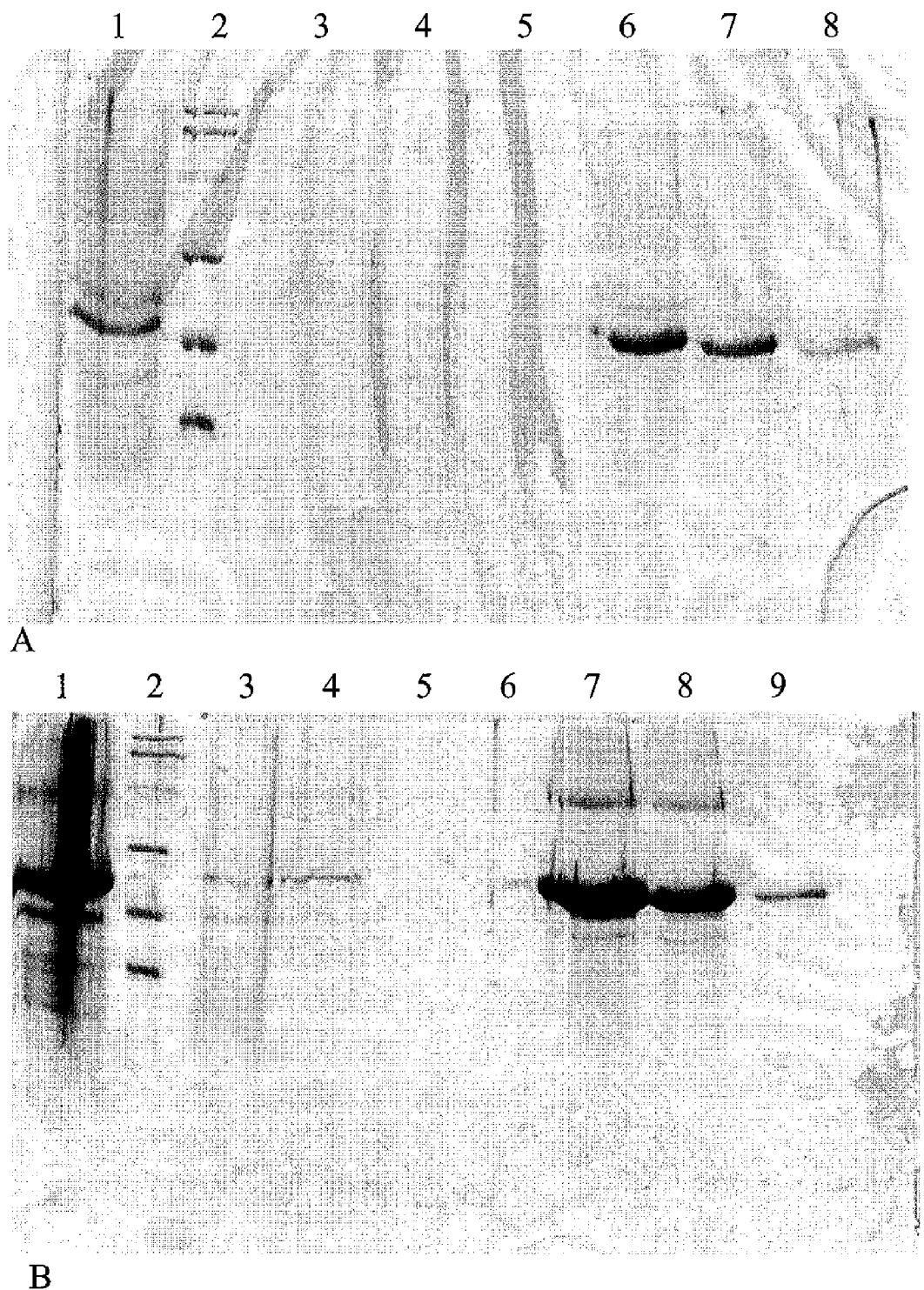
FIG. 11 shows Coomassie-stained SDS-PAGES of fractions from the purification of A) rdBMP-6 and B) rdBMP-6 with heparin binding site. The bands represent 1) starting material, 2) standard, 3) flow through, 4) first wash, 5) second wash, 6) elution 1, 7) elution 2, 8) elution 3 and in addition 9) elution 4 in rd-BMP-6-HBS.

The next purification step was the immobilized metal affinity chromatography (IMAC). After the elution of the column with pH gradient, the purity of rdBMP-6 measured from the SDS-PAGE was up to 75%. The isolated protein with the mature part of rdBMP-6 had a MW of 20,300 Da as shown by the electrophoretic mobility on SDS-PAGE under reducing conditions (FIG. 11).

Purification of rdBMP-6-HBS

Recombinant reindeer rdBMP-6-HBS protein was overexpressed in *E. coli* and produced as inclusion bodies (IBs). After the wash treatment, isoelectric point precipitation and solubilization of the inclusion bodies the content of recombinant reindeer rdBMP-6-HBS was 85%.

The next purification step was the immobilized metal affinity chromatography (IMAC). After the elution of the column with pH gradient, the purity of rdBMP-6-HBS measured from the SDS-PAGE was up to 75%. The isolated protein with the mature part of rdBMP-6-HBS had a MW of 21,600 Da as shown by the electrophoretic mobility on SDS-PAGE under reducing conditions (FIG. 11).

Refolding and Activity Tests of rdBMP-6 and rdBMP-6-HBS

The in vitro refolding of the denatured rdBMP-6 and rdBMP-6-HBS protein was quantitated by measuring of the refold dimer of the protein on Coomassie Brilliant Blue stained gels densitometrically. The amount of refolding measured by non-reducing SDS-PAGE was by both proteins 50%.

The osteoinductive activity induced by rdBMP-6 was increased in dose dependent manner (Table 2). When compared to its human counterpart the recombinant reindeer BMP-6 was proven to be more potent inducer of bone formation. The bone forming activity of reindeer BMP-6-HBS seemed to be in proportion to rdBMP-6 whereas bovine BMP-6 was responded only at the biggest amount studied.

Refolding and Activity Tests of rdBMP-3c/138, rdBMP-3c/110, HBSrd3c/138 and HBSrd3c/110

The in vitro refolding of the denatured rdBMP-3c proteins was quantified by measuring of the refold dimer of the protein on Coomassie Brilliant Blue stained gels densitometrically. The amount of refolding measured by non-reducing SDS-PAGE was by the rdBMP-3c proteins without HBS 50% and by the HBSrdBMP-3c over 70%.

The osteoinductive activity induced by rdBMP-3c proteins without HBS was increased in dose dependent manner at least until 5 mg. When compared the biological activity of BMP-3c/138 to BMP-3c/110 it seemed, that BMP-3c/110 was more potent inducer of bone formation. The fact, that refolding was 20% higher by the rdBMP-3c with HBS than without HBS, makes the HBSrdBMP-3c of great value (data not shown).

Purification of HBSBMP-4 Protein

Recombinant reindeer HBSrdBMP-4 protein was slightly overexpressed in *E. coli* and produced as inclusion bodies (IBs). After the wash treatment, isoelectric point precipitation and solubilization of the inclusion bodies, they were next purified with the affinity chromatography (IMAC and heparin). After the elution of the columns, the purity of HBSrdBMP-4 measured from the SDS-PAGE was up to 75%. The isolated proteins with the mature part of HBSrdBMP-4 had a MW of 17,700 Da as shown by the electrophoretic mobility on SDS-PAGE under reducing conditions.

Refolding and Activity Tests of HBSrdBMP-4

The in vitro refolding of the denatured HBSrdBMP-4 protein was quantified by measuring of the refold dimer of the protein on Coomassie Brilliant Blue stained gels densitometrically. The amount of refolding measured by non-reducing SDS-PAGE was by HBSBMP-4 protein over 60%.

HBSrdBMP-4 protein produced in *E. coli* TOP10 expression system showed biological activity when implanted in mouse tight muscle pouch. Furthermore, the refolding of the rdBMP-4 with HBS was significantly higher than without HBS, which makes the HBSrdBMP-4 of great value (data now shown).

This invention has been described with an emphasis upon some of the preferred embodiments and applications. However, it will be apparent for those skilled in the art that variations in the disclosed embodiments can be prepared and used and that the invention can be practiced otherwise than as specifically described herein within the scope of the following claims.

The invention claimed is:

1. An isolated bone morphogenetic protein (BMP) having osteogenic activity, comprising (a) the amino acid sequence as set forth in SEQ ID NO: 1, or (b) an amino acid sequence that is at least 70 percent identical to the amino acid sequence as set forth in SEQ ID NO: 1 and has the consensus amino acid sequence P-G/S/N-R/K-R/H-R/K-Q/N-Q-A/S/N-R-N/S-R/A/K-S/A-T/S/N-P, or an osteogenic fragment of said BMP.

2. The bone morphogenetic protein of claim 1, comprising amino acids 3-16 of SEQ ID NO: 1.

3. The bone morphogenetic protein of claim 2, comprising the amino acid sequence of SEQ ID NO: 1.

4. The bone morphogenetic protein of claim 1, further comprising the BMP propeptide of SEQ ID NO: 2.

5. An isolated DNA molecule, encoding the BMP of claim 1.

6. A nucleotide vector, comprising the isolated DNA molecule of claim 5.

7. A recombinant host cell, comprising the nucleotide vector of claim 6.

8. The recombinant host cell of claim 7, wherein the cell is *E. coli* TOP10, Origami B (DE3) or Rosetta (DE3).

9. A pharmaceutical composition, comprising the BMP of claim 1.

10. The pharmaceutical composition of claim 9, comprising said BMP as homodimer or as heterodimer together with another bone morphogenetic protein.

11. The pharmaceutical composition of claim 9, further comprising another bone morphogenetic protein, epidermal growth factor, fibroblast growth factor or transforming growth factor.

12. An osteogenic device, comprising the BMP of claim 1.

13. The osteogenic device of claim 12, comprising said BMP as homodimer or as heterodimer together with another bone morphogenetic protein.

14. The osteogenic device of claim 12, further comprising another bone morphogenetic protein, epidermal growth factor, fibroblast growth factor or transforming growth factor.

15. The osteogenic device of claim 12, comprising a biocompatible matrix.

16. The osteogenic device of claim 15, wherein said biocompatible matrix comprises calcium phosphate, carboxy methyl cellulose or collagen or combinations thereof.

17. A method for inducing the formation of bone, cartilage, tendon or tooth in vitro or in vivo, the method comprising treating said bone, cartilage, tendon or tooth with the BMP of claim 1.

18. A method for treating disorders related to bone, cartilage, tendon or tooth, wherein regeneration, repair or growth thereof is desired, the method comprising administering the bone morphogenetic protein of claim 1 to a patient suffering from said disorder.

19. A method for improving the expression of recombinant BMP protein in a bacterial host, comprising adding a heparin binding site containing the amino acid sequence AKHKQRKRGT (SEQ ID NO: 5) to the amino terminus of said protein to be expressed.

20. A method for enhancing the biological activity of recombinant BMP protein, comprising adding a heparin binding site containing the amino acid sequence AKHKQRKRGT (SEQ ID NO: 5) to the amino terminus of said protein.

21. The method of claim 19, wherein the recombinant BMP protein is selected from BMP-3, BMP-4 and BMP-6 proteins.

22. A method for producing a recombinant BMP protein having lowered immunogenicity, comprising expressing the BMP of claim 1 in a bacterial host.

23. The method of claim 22, wherein the bacterial host is *Escherichia coli*.

24. The bone morphogenetic protein of claim 1, further comprising a heparin binding site containing the amino acid sequence AKHKQRKRGT (SEQ ID NO: 5) at the amino terminus of the protein.

* * * * *